United States Patent
Sorimoto

(10) Patent No.: US 11,060,852 B2
(45) Date of Patent: Jul. 13, 2021

(54) THREE-DIMENSIONAL SCANNER AND PROBE

(71) Applicant: J. MORITA MFG. CORP., Kyoto (JP)

(72) Inventor: Keisuke Sorimoto, Kyoto (JP)

(73) Assignee: J. MORITA MFG. CORP., Kyoto (JP)

( * ) Notice: Subject to any disclaimer, the term of this patent is extended or adjusted under 35 U.S.C. 154(b) by 0 days.

(21) Appl. No.: 16/340,976

(22) PCT Filed: Mar. 8, 2018

(86) PCT No.: PCT/JP2018/008961
§ 371 (c)(1),
(2) Date: Apr. 10, 2019

(87) PCT Pub. No.: WO2018/168635
PCT Pub. Date: Sep. 20, 2018

(65) Prior Publication Data
US 2019/0293414 A1    Sep. 26, 2019

(30) Foreign Application Priority Data

Mar. 13, 2017   (JP) .............................. JP2017-047210

(51) Int. Cl.
*G01B 11/25*   (2006.01)
*A61B 5/107*   (2006.01)
(Continued)

(52) U.S. Cl.
CPC ........ *G01B 11/2513* (2013.01); *A61B 5/1077* (2013.01); *A61B 5/1079* (2013.01);
(Continued)

(58) Field of Classification Search
CPC ..... G01B 11/2513; G01B 11/25; G01B 11/24; G01B 11/2518; G01B 11/2504;
(Continued)

(56) References Cited

U.S. PATENT DOCUMENTS

| | | | |
|---|---|---|---|
| 5,071,229 A | | 12/1991 | Oaki et al. |
| 5,178,536 A | * | 1/1993 | Werly ...................... A61B 1/24 348/66 |

(Continued)

FOREIGN PATENT DOCUMENTS

| | | |
|---|---|---|
| EP | 2213223 A1 | 8/2010 |
| EP | 3462236 A1 | 4/2019 |

(Continued)

OTHER PUBLICATIONS

International Search Report issued in Application No. PCT/JP2018/008961, dated May 15, 2018 (2 pages).

(Continued)

*Primary Examiner* — Mohamed K Amara
(74) *Attorney, Agent, or Firm* — Osha Bergman Watanabe & Burton LLP

(57) ABSTRACT

A three-dimensional scanner for obtaining shape information of an object body includes a light source unit, a varifocal unit, a reference unit, a light path length adjustment unit, an optical sensor, and a control unit. The varifocal unit is able to change a focal position, and both of light from the light source unit to the optical sensor via an object body and light from the light source unit to the optical sensor via the reference unit travel at least once. The control unit determines a condition of varifocal unit based on light has been reflected on reference unit and detected by a part of optical sensor, and calculates the shape information of the object body from light detected by the optical sensor using information of the condition of the varifocal unit that has been determined.

16 Claims, 13 Drawing Sheets

(51) Int. Cl.
  *G02B 7/36* (2021.01)
  *G03B 13/36* (2021.01)
  *G02B 7/28* (2021.01)
  *G01B 11/24* (2006.01)

(52) U.S. Cl.
  CPC .............. *G01B 11/24* (2013.01); *G01B 11/25* (2013.01); *G01B 11/2518* (2013.01); *G02B 7/28* (2013.01); *G02B 7/36* (2013.01); *G03B 13/36* (2013.01)

(58) Field of Classification Search
  CPC ... G02B 7/28; G02B 7/36; G02B 3/14; G02B 21/0028; G02B 21/006; G02B 21/0064; G02B 23/2446; G02B 23/2461; G02B 23/26; G02B 27/0025; A61B 5/1077; A61B 5/1079; A61B 5/0088; A61B 5/0068; A61B 1/06; A61B 1/24; A61B 5/1075; A61B 5/1076; G03B 13/36; A61C 9/0053; A61C 9/0066; A61C 1/088; H04N 13/296; H04N 5/2256; H04N 5/23212; H04N 9/045
  See application file for complete search history.

(56) References Cited

U.S. PATENT DOCUMENTS

| | | | | |
|---|---|---|---|---|
| 5,562,448 | A * | 10/1996 | Mushabac | A61C 13/0004 433/215 |
| 5,604,344 | A | 2/1997 | Finarov | |
| 5,607,305 | A * | 3/1997 | Andersson | A61C 9/002 433/223 |
| 5,737,084 | A * | 4/1998 | Ishihara | G01B 11/026 356/609 |
| 6,382,975 | B1 * | 5/2002 | Poirier | A61C 1/084 433/173 |
| 6,402,707 | B1 * | 6/2002 | Ernst | A61B 5/1076 600/590 |
| 7,092,107 | B2 * | 8/2006 | Babayoff | A61B 1/00096 356/609 |
| 7,312,879 | B2 * | 12/2007 | Johnston | A61B 5/0084 250/208.1 |
| 7,616,987 | B2 * | 11/2009 | Premachandran | A61B 5/0088 600/473 |
| 8,556,625 | B2 * | 10/2013 | Lovely | A61B 1/063 433/29 |
| 8,643,946 | B2 * | 2/2014 | Westphal | G02B 21/244 359/368 |
| 9,089,382 | B2 * | 7/2015 | Hochman | A61B 1/24 |
| 10,070,791 | B2 * | 9/2018 | Liang | A61B 1/0607 |
| 10,159,547 | B2 * | 12/2018 | Mormann | A61C 9/0066 |
| 10,251,736 | B2 * | 4/2019 | Nakai | A61C 19/041 |
| 10,772,506 | B2 * | 9/2020 | Atiya | G01B 11/245 |
| 2003/0001071 | A1 * | 1/2003 | Mandella | G01B 9/02003 250/201.3 |
| 2004/0036838 | A1 * | 2/2004 | Podoleanu | A61B 3/102 351/206 |
| 2004/0186382 | A1 * | 9/2004 | Modell | A61B 5/0075 600/473 |
| 2007/0252074 | A1 * | 11/2007 | Ng | G02B 27/0075 250/208.1 |
| 2007/0296959 | A1 | 12/2007 | Schwotzer | |
| 2009/0021724 | A1 * | 1/2009 | Mahadevan-Jansen | A61B 5/445 356/73 |
| 2009/0131921 | A1 * | 5/2009 | Kurtz | A61F 9/0084 606/4 |
| 2009/0268161 | A1 * | 10/2009 | Hart | A61B 3/102 351/208 |
| 2011/0043661 | A1 * | 2/2011 | Podoleanu | G01B 9/02069 348/239 |
| 2011/0299034 | A1 * | 12/2011 | Walsh | A61B 3/0091 351/206 |
| 2012/0092461 | A1 | 4/2012 | Fisker et al. | |
| 2012/0092678 | A1 * | 4/2012 | Babayoff | A61B 1/247 356/601 |
| 2013/0265545 | A1 * | 10/2013 | Buckland | A61B 3/102 351/206 |
| 2015/0037750 | A1 | 2/2015 | Moalem | |
| 2015/0201878 | A1 * | 7/2015 | Chen | A61B 5/413 600/425 |
| 2016/0045291 | A1 | 2/2016 | Verker et al. | |
| 2017/0202483 | A1 * | 7/2017 | Sorimoto | A61B 1/00009 |
| 2019/0223732 | A1 * | 7/2019 | Fan | A61B 5/682 |
| 2019/0343377 | A1 * | 11/2019 | Fan | A61B 1/24 |

FOREIGN PATENT DOCUMENTS

| | | |
|---|---|---|
| EP | 3503524 A1 | 6/2019 |
| EP | 3503525 A1 | 6/2019 |
| JP | H07-239216 A | 9/1995 |
| JP | 2008-523370 A | 7/2008 |
| JP | 2010-43954 A | 2/2010 |
| JP | 2013-180120 A | 9/2013 |
| JP | 2014-142183 A | 8/2014 |
| JP | 5654583 B2 | 1/2015 |
| JP | 2016-534334 A | 11/2016 |

OTHER PUBLICATIONS

Written Opinion issued in International Application No. PCT/JP2018/008961, dated May 15, 2018 (3 pages).

Extended European Search Report issued in European Application No. 18766614.4, dated Dec. 7, 2020 (9 pages).

* cited by examiner

THREE-DIMENSIONAL SCANNER AND PROBE

TECHNICAL FIELD

The present invention relates to a three-dimensional scanner for obtaining shape information of an object body, and a probe detachable from an opening of the three-dimensional scanner.

BACKGROUND ART

In the field of dentistry, a three-dimensional scanner (oral scanner) for obtaining a three-dimensional shape of a tooth has been developed in order to design a prosthesis or the like digitally on a computer (Japanese Patent No. 5654583). The three-dimensional scanner disclosed in Japanese Patent No. 5654583 is a handheld scanner for obtaining a three-dimensional shape of an object body using principles of a focusing method. Specifically, according to this three-dimensional scanner, light having a linear or checkerboard design pattern (hereinafter also referred to as a pattern) is projected onto a surface of an object body, a best focused distance is obtained from a plurality of images of the pattern taken while changing a focusing position, and thus a three-dimensional shape of the object body is obtained.

In other words, this three-dimensional scanner requires a varifocal unit for changing the focus of the pattern projected onto the object body at a high speed. Here, it is possible to obtain the three-dimensional shape using principles of a triangulation method or white light interferometry, other than the focusing method. Unlike the focusing method, these principles do not use the focus, and therefore it is basically possible to perform three-dimensional measurement without any varifocal unit.

However, even with those principles, providing functions of zoom adjustment and focus adjustment for an optical system improves conveniences in measurement. In this case, a three-dimensional scanner using principles other than the focusing method also requires a varifocal unit for changing a focal position of light from a light source.

CITATION LIST

Patent Literature

PTL 1: Japanese Patent No. 5654583

SUMMARY OF INVENTION

Technical Problems

However, according to this three-dimensional scanner, it is necessary to correctly grasp a focal position of the projected pattern that has been projected to obtain an accurate three-dimensional shape. Further, even in a case in which the three-dimensional shape is obtained using principles such as the triangulation method and the white light interferometry other than the focusing method, if the optical system includes a varifocal unit, it is necessary to correctly grasp the focal position to obtain an accurate three-dimensional shape. In particular, when a liquid lens is used for a varifocal unit, it is difficult to correctly grasp the focal position as the liquid lens has hysteresis characteristics where its focal position is different between a case in which an applied voltage value is increased and a case in which an applied voltage value is decreased. Here, in order to correctly grasp the focal position of the project pattern, it is necessary to correctly grasp conditions of the varifocal unit. Examples of the condition of the varifocal unit include a position of the lens, a curvature shape of the lens, and a refractive index of the lens. The condition of the varifocal unit may change depending on ambient temperature, deformation with age of the varifocal unit, and the like, in addition to the hysteresis characteristics. A three-dimensional scanner applicable to manufacturing of dental prostheses requires extremely high measurement accuracy in a practical sense, and in particular, it is necessary to correctly grasp conditions of a varifocal unit.

The present invention has been made in order to address the above problems, and an object of the present invention is to provide a three-dimensional scanner capable of correctly grasping conditions of a varifocal unit and obtaining an accurate three-dimensional shape, and a probe.

Solutions to Problems

A three-dimensional scanner according to the present invention is a three-dimensional scanner for obtaining shape information of an object body, the scanner including: a light source unit; a detection unit for detecting light from the light source unit, the light being reflected on the object body; a reference unit for being irradiated with a part of the light from the light source unit; a varifocal unit capable of changing a focal position, the varifocal unit being a unit through which both of light from the light source unit to the detection unit via the object body and light from the light source unit to the detection unit via the reference unit travel at least once; a light path length adjustment unit for adjusting a length of a light path from the object body to the detection unit and a length of a light path from the reference unit to the detection unit; a determination unit for determining a condition of the varifocal unit based on light that has been reflected on the reference unit and detected by a part of the detection unit; and a calculation unit for calculating shape information of the object body from the light detected by the detection unit, using information of the condition of the varifocal unit determined by the determination unit.

A probe according to the present invention is a probe for emitting light from a light source unit to an object body, and for receiving light reflected on the object body, the probe being detachable from an opening of a three-dimensional scanner, the probe including: a reference unit for being irradiated with a part of the light from the light source unit; and a housing in which the reference unit is provided, wherein the three-dimensional scanner includes: a detection unit for detecting the light from the light source unit, the light being reflected on the object body; a varifocal unit capable of changing a focal position, the varifocal unit being a unit through which both of light from the light source unit to the detection unit via the object body and light from the light source unit to the detection unit via the reference unit travel at least once; a light path length adjustment unit for adjusting a length of a light path from the object body to the detection unit and a length of a light path from the reference unit to the detection unit; a determination unit for determining a condition of the varifocal unit based on light that has been reflected on the reference unit and detected by a part of the detection unit; and a calculation unit for calculating shape information of the object body from the light detected by the detection unit, using information of the condition of the varifocal unit determined by the determination unit.

Advantageous Effects of Invention

The three-dimensional scanner according to the present invention determines the condition of the varifocal unit based on the light that has been reflected on the reference unit and detected by a part of the detection unit, and therefore the scanner is able to correctly grasp the condition of the varifocal unit and obtain the accurate three-dimensional shape. Further, the probe according to the present invention includes the reference unit, within its housing, for determining the condition of the varifocal unit, and therefore the probe allows the three-dimensional scanner to correctly grasp the condition of the varifocal unit and to obtain the accurate three-dimensional shape.

DESCRIPTION OF EMBODIMENTS

Hereinafter, embodiments according to the present invention will be described with reference to the drawings.

Embodiment 1

A three-dimensional scanner according to Embodiment 1 of the present invention is a three-dimensional scanner (oral scanner) for obtaining a three-dimensional shape of a tooth in the mouth. However, the three-dimensional scanner according to the present invention is not limited to the oral scanner, and can be applied to other types of the three-dimensional scanner having a similar configuration.

As one example, other than the interior of the mouth, the three-dimensional scanner according to the present invention is applicable to a three-dimensional scanner capable of taking images of an interior of a person's ear and obtaining a three-dimensional shape of an interior of an outer ear.

{Configuration of Three-Dimensional Scanner}

Figure 1:
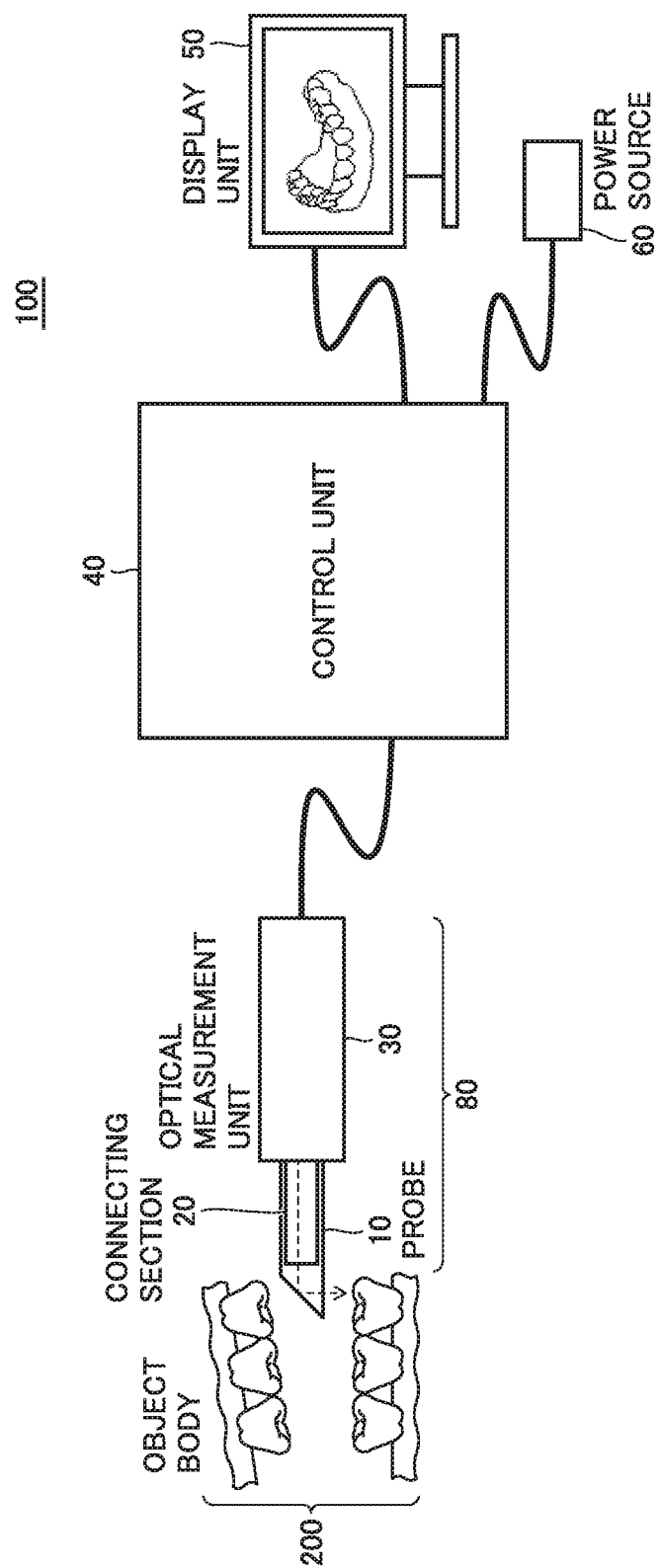
FIG. 1 is a block diagram illustrating a configuration of a three-dimensional scanner according to Embodiment 1 of the present invention.

FIG. 1 is a block diagram illustrating a configuration of a three-dimensional scanner 100 according to Embodiment 1 of the present invention. Three-dimensional scanner 100 shown in FIG. 1 includes a probe 10, a connecting section 20, an optical measurement unit 30, a control unit 40, a display unit 50, and a power unit 60. Probe 10 is inserted into the mouth, projects light having a pattern (hereinafter also referred to as a pattern) onto a tooth as an object body 200, and guides reflection light reflected from object body 200 on which the pattern is projected, to optical measurement unit 30. Further, as probe 10 is detachable from optical measurement unit 30, it is possible to perform sterilization (for example, a treatment in an environment with high temperature and high humidity), as infection control, to probe 10 that may be brought into contact with a living body after removing the probe from optical measurement unit 30. While sterilizing an entire device of the three-dimensional scanner has a disadvantage that the duration of the device's life becomes shorter as it includes a number of optical and electronic components, this disadvantage does not occur when only probe 10 is removed and sterilized. Connecting section 20 is a part that protrudes from optical measurement unit 30, and has a shape that is fittable with probe 10. Connecting section 20 may include a lens system for guiding light collected by probe 10 to optical measurement unit 30, and optical components such as a cover glass, an optical filter, and a retardation plate (quarter wavelength plate).

Optical measurement unit 30 projects a pattern onto object body 200 via probe 10, and takes an image of the projected pattern. While not illustrated, optical measurement unit 30 includes an optical component (pattern generating element) for generating a pattern to be projected onto object body 200, a light source, a lens component for forming an image of the pattern on a surface of object body 200, a varifocal unit capable of changing a focal position, and an optical sensor for taking an image of the projected pattern (such as a CCD image sensor or a CMOS image sensor). Here, while optical measurement unit 30 is described to have a configuration for obtaining a three-dimensional shape using principles of a focusing method, optical measurement unit 30 is not limited to such a configuration, and may have a configuration for obtaining a three-dimensional shape using principles of a method such as confocal method, triangulation method, white light interferometry, stereo method, photogrammetry, SLAM method (Simultaneous Localization and Mapping), and optical coherence tomography (Optical Coherence Tomography: OCT). In other words, optical measurement unit 30 is applicable to any configuration using any principles, as long as the configuration is such that a varifocal unit is included and a three-dimensional shape is obtained using an optical method. Here, probe 10, connecting section 20, and optical measurement unit 30 constitute a handpiece 80 for taking an image of an interior of the mouth.

Control unit 40 controls an operation of optical measurement unit 30, and processes an image taken by optical measurement unit 30 to obtain a three-dimensional shape. Control unit 40 includes a CPU (Central Processing Unit) as a control center, a ROM (Read Only Memory) that records programs and control data for causing the CPU to be operated, a RAM (Random Access Memory) that serves as a work area of the CPU, an input-output interface for maintaining consistency with signals from peripheral devices, and the like. Further, control unit 40 is able to output the obtained three-dimensional shape to display unit 50, and receives information such as setting of optical measurement unit 30 via an unillustrated input device or the like. Here, at least of a part of calculation for processing taken images and obtaining a three-dimensional shape may be realized as software by the CPU of control unit 40, or as hardware performing the processes separately from the CPU. Further, at least a part of processing units such as the CPU and the hardware may be incorporated within optical measurement unit 30. Moreover, while FIG. 1 shows the components (30, 40, 50, and 60) of three-dimensional scanner 100 as being connected by cables (thick lines in the figure), a part or all of the connection may be realized by wireless communication. In addition, if control unit 40 is enough small and light to be held by one hand, control unit 40 and optical measurement unit 30 may be combined and configured as a single handpiece.

Display unit 50 is a display device for displaying results of measurement of the three-dimensional shape of object body 200 obtained by control unit 40. Further, display unit 50 is also usable as a display device for displaying other information such as configuration information of optical measurement unit 30, patient information, and a startup status, an operation manual, and a help screen of the scanner. As display unit 50, a standing liquid crystal display and a wearable display of head-mounted type or a glass type can be used, for example. Further, more than one display unit 50 may be provided, and it is possible to display results of the measurement of the three-dimensional shape and other information at the same time or separately on the plurality of display units 50. Power unit 60 is a device for supplying electric power for driving optical measurement unit 30 and control unit 40. Power unit 60 may be provided outside control unit 40 as illustrated in FIG. 1, or may be provided inside control unit 40. Moreover, more than one power unit 60 may be provided so that electric power may be separately fed to control unit 40, optical measurement unit 30, and display unit 50.

{Optical Configuration within Handpiece}

Figure 2:
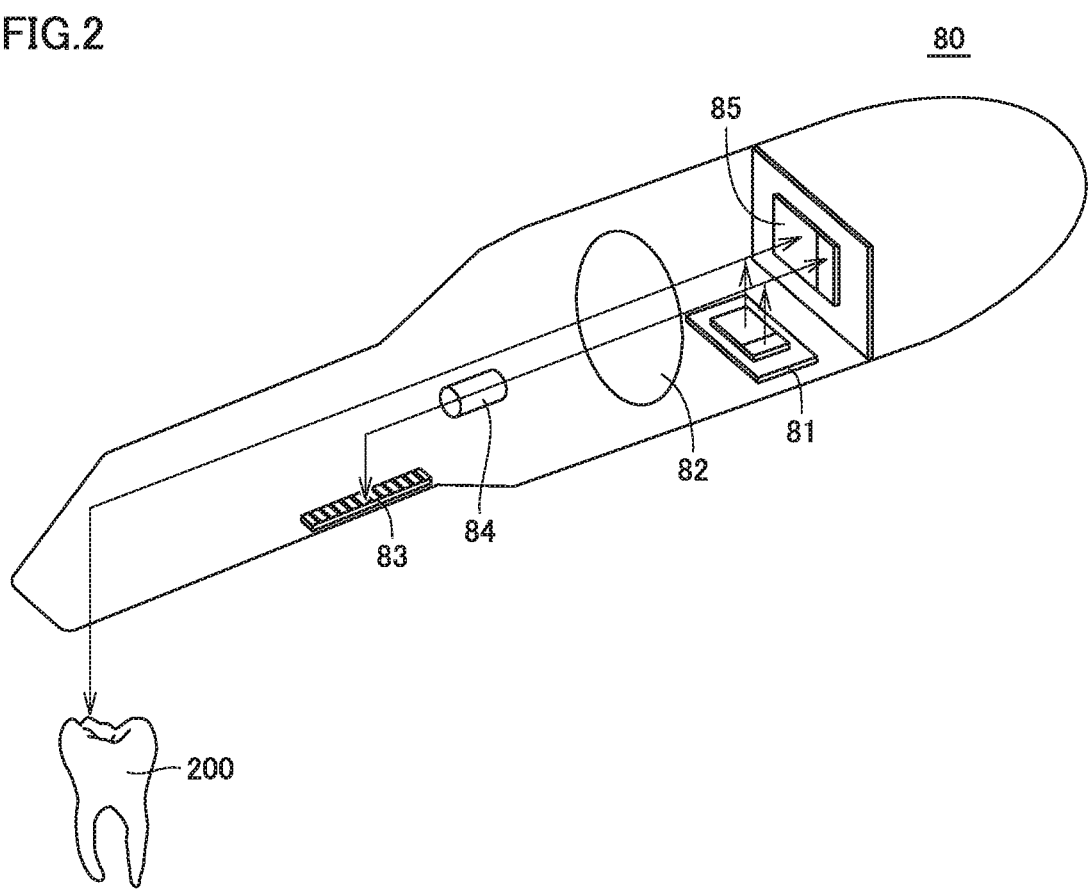
FIG. 2 is a schematic diagram illustrating a configuration of an optical system within a handpiece according to Embodiment 1 of the present invention.

Next, a configuration of an optical system within the handpiece will be described more in detail. FIG. 2 is a schematic diagram illustrating a configuration of an optical system within handpiece 80 according to Embodiment 1 of the present invention. First, handpiece 80 includes a light source unit 81, a varifocal unit 82, a reference unit 83, a light path length adjustment unit 84, and an optical sensor 85. In addition to these components, handpiece 80 also includes other components as needed, such as a beam splitter for splitting light from light source unit 81 to object body 200 and light from object body 200 to optical sensor 85, a lens system, and a light reflector for reflecting light to object body 200 and reference unit 83. However, configurations of these components are neither illustrated in FIG. 2, nor described in detail.

Light output form light source unit 81 irradiates object body 200 through varifocal unit 82, and is reflected on object body 200. The light reflected on object body 200 travels through varifocal unit 82, and is detected by optical sensor 85. When a three-dimensional shape is obtained using techniques of the focusing method, light that has passed through the pattern generating element (not illustrated) provided between light source unit 81 and object body 200 is projected upon object body 200, and the light from object body 200 is detected by optical sensor 85 while changing conditions of varifocal unit 82 (a focal position of the projected pattern of varifocal unit 82). Control unit 40 illustrated in FIG. 1 calculates shape information of object body 200 based on the condition of varifocal unit 82 and results of the detection by optical sensor 85 at this position. Therefore, it is not possible to obtain an accurate three-dimensional shape without correctly grasping the condition of varifocal unit 82.

Figure 3A:
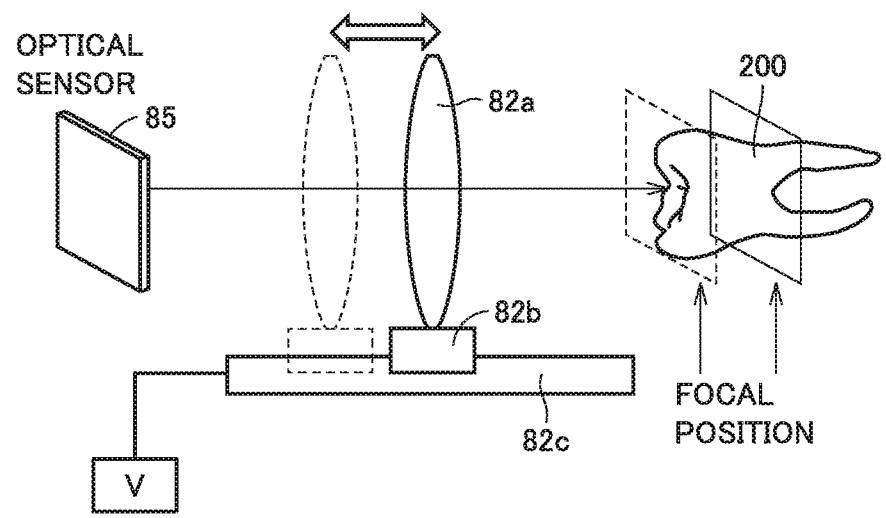
FIGS. 3(a)-3(b) are schematic diagrams illustrating a configuration of a varifocal unit according to Embodiment 1 of the present invention.
Figure 3B:
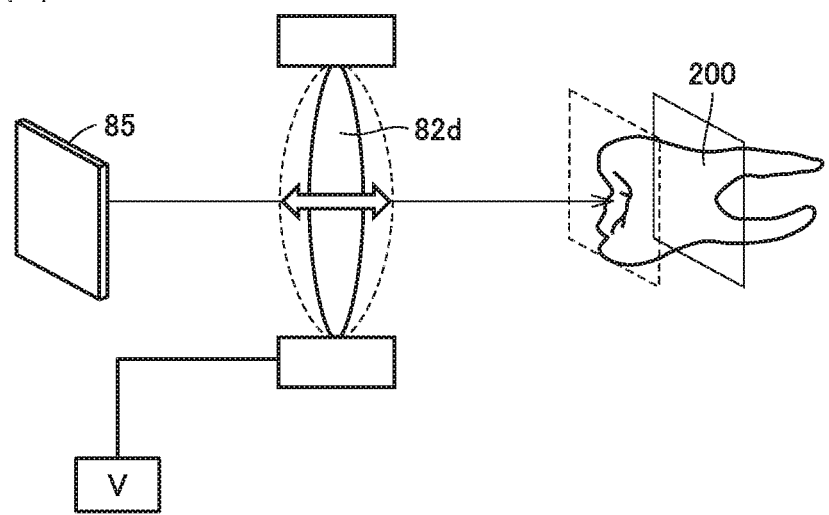

Here, examples of the configuration of varifocal unit 82 include a configuration in which the focal position of the project pattern is changed by mechanically moving the position of the lens, and a configuration in which a varifocal lens (for example, liquid lens) that does not mechanically move the position of the lens is used. The above configurations are described respectively with reference to the drawings. FIGS. 3(a)-3(b) are schematic diagrams illustrating a configuration of the varifocal unit according to Embodiment 1 of the present invention. Here, a reference sign V in the figure indicates a controller for supplying electric power and control signals to varifocal unit 82. With the varifocal unit illustrated in FIG. 3(a), a focus lens 82a is fixed to a slider 82b, and the project pattern and the focal position of optical sensor 85 are changed by moving slider 82b along a rail 82c that extends along a light axis. While the varifocal unit illustrated in FIG. 3(a) mechanically moves focus lens 82a by supplying electric power to slider 82b, it is necessary to provide a configuration in which a gauge is separately provided for focus lens 82a and the gauge is optically detected, in order to know the position of focus lens 82a on the light axis. Providing this configuration within handpiece 80 requires a space for accommodating the configuration, resulting in a problem in which a size of handpiece 80 itself is increased.

On the other hand, the varifocal unit illustrated in FIG. 3(b) employs a liquid lens 82d as a varifocal lens that does not mechanically move the position of the lens. One example of liquid lens 82d has such a configuration in which an electrode is provided on a side of a container enclosing aqueous solution and oil, and the boundary between the aqueous solution and the oil is changed by applying a voltage on the electrode to change the focal position (FIG. 3(b) schematically shows liquid lens 82d as a single biconvex lens, and details such as the aqueous solution and the oil are not shown). Therefore, the varifocal unit illustrated in FIG. 3(b) does not require the configuration of providing a gauge for the lens to perform optical detection. However, liquid lens 82d has a problem that it is difficult to correctly grasp the focal position as the liquid lens has hysteresis characteristics where its focal position is different between a case in which an applied voltage value is increased and a case in which an applied voltage value is decreased. Therefore, this embodiment provides a configuration with which the focal position can be correctly grasped and a reduced size can be provided even when varifocal unit 82 takes either of the configuration in which the position of the lens is moved mechanically, and the configuration in which the position of the lens is not moved mechanically.

Here, examples of the condition of varifocal unit 82 of the configuration in which the position of the lens is moved mechanically include a position of the lens, a refractive index of the lens, and a curvature shape of the lens. Further, examples of the condition of varifocal unit 82 of the configuration in which the position of the lens is not moved mechanically include a refractive index of the lens, and a curvature shape of the lens. In the following description, reference unit 83 having a known design pattern is prepared, and the condition of varifocal unit 82 is correctly grasped using results of taken images of the design pattern provided for reference unit 83. Further, in the following description, a liquid lens is used as varifocal unit 82. However, varifocal unit 82 is not limited to a liquid lens, and may take the configuration in which the position of the lens is moved mechanically. Moreover, while in the following description, the condition of varifocal unit 82 is indirectly grasped using reference unit 83, it should be understood that the condition of varifocal unit 82 can be directly grasped by providing another configuration in which values of a refractive index of the lens and a curvature shape of the lens are directly measured based on light traveling through varifocal unit 82 and the like.

Referring back to FIG. 2, a specific method for correctly grasping the condition of varifocal unit 82 will be described. First, light output from a part of light source unit 81 irradiates reference unit 83 through varifocal unit 82, and is reflected on reference unit 83. The light reflected on reference unit 83 travels through varifocal unit 82, and is detected by a part of optical sensor 85. Here, as reference unit 83 is provided within a housing of handpiece 80, a light path from the part of light source unit 81 to the part of optical sensor 85 via reference unit 83 is shorter than a light path from light source unit 81 to optical sensor 85 via object body 200. Therefore, light path length adjustment unit 84 for adjusting a length of the light path from light source unit 81 to optical sensor 85 via object body 200 and a length of the light path from the part of light source unit 81 to the part of optical sensor 85 via reference unit 83 is provided along the light path from the part of light source unit 81 to the part of optical sensor 85 via reference unit 83.

Light path length adjustment unit 84 may be any optical element that is able to adjust the length of the light path along the light path from the part of light source unit 81 to the part of optical sensor 85 via reference unit 83, and examples of light path length adjustment unit 84 include a glass block, a light guide, a lens or a lens array, an offset mirror/prism, a dichroic mirror, a delay line, and a pentaprism. By making the lengths of the light paths substantially match using light path length adjustment units 84, it is possible to take images that are generally focused by the optical sensor for both of object body 200 and reference unit 83. Specifically, it is possible to make correspondence between a focusing position for object body 200 and a focusing position for reference unit 83. Therefore, it is possible to correctly grasp the condition of varifocal unit 82 by analyzing images of reference unit 83 taken using the part of optical sensor 85 to obtain the focusing position for reference unit 83.

Figure 4A:
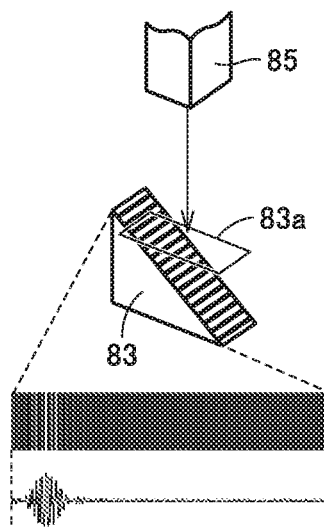
FIGS. 4(a)-4(c) are schematic diagrams illustrating a configuration of a reference unit according to Embodiment 1 of the present invention.
Figure 4B:
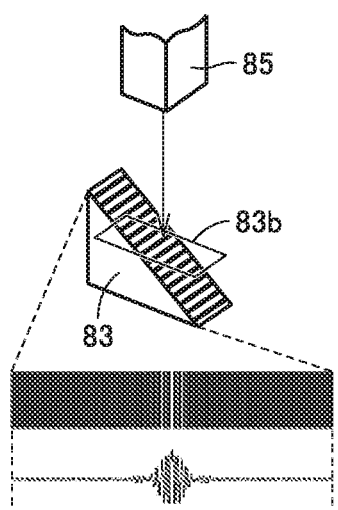
Figure 4C:
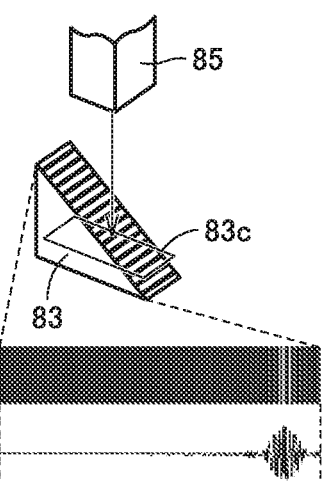

A configuration of reference unit 83 will be described with reference to the drawings. FIGS. 4(*a*)-4(*c*) are schematic diagram illustrating a configuration of a reference unit according to Embodiment 1 of the present invention. Reference unit 83 illustrated in FIGS. 4(*a*)-4(*c*) is a flat plate having a striped design pattern, and disposed so as to be inclined with respect to a light axis of optical sensor 85. Therefore, when the condition of varifocal unit 82 that are not illustrated is changed to bring a focus to a position 83*a* on an upper section of reference unit 83 (FIG. 4(*a*)), an image taken by the part of optical sensor 85 shows the striped pattern only at a position on the left side of the image. As the remaining portion of the image is out of focus, the striped design pattern is not shown as the contrast of the pattern is vague due to image blur. By analyzing this image, it is possible to obtain a signal showing a waveform only at the position on the left side of the image. As examples of a method for analyzing an image to obtain a signal, the striped pattern that appears at different portions of images depending on the condition of varifocal unit 82 can be analyzed using a known algorithm such as a differentiation method, a pattern matching method, and an envelope detection method. Here, a position of the waveform in the signal obtained from the striped pattern and the condition of varifocal unit 82 correspond on a one-on-one basis. Control unit 40 illustrated in FIG. 1 is able to correctly grasp the condition of varifocal unit 82 based on this signal. In other words, control unit 40 serves as a determination unit for determining the condition of varifocal unit 82 based on light reflected on reference unit 83 that has been detected by the part of optical sensor 85. Further, control unit 40 calculates shape information of object body 200 from an image taking light reflected on object body 200 that has been detected by optical sensor 85, using information of the condition of varifocal unit 82 that has been determined.

Similarly, when the condition of varifocal unit 82 that are not illustrated is changed to bring a focus to a position 83*b* on a middle section of reference unit 83 (FIG. 4(*b*)), an image taken by optical sensor 85 shows the striped pattern only at a position at the center of the image. By analyzing this image, it is possible to obtain a signal showing a waveform only at the position at the center of the figure. Further, when the condition of varifocal unit 82 that is not illustrated is changed to bring a focus to a position 83*c* on a lower section of reference unit 83 (FIG. 4(*c*)), an image taken by the part of optical sensor 85 shows the striped pattern only at a position on the right side of the image. By analyzing this image, it is possible to obtain a signal showing a waveform only at the position on the right side of the figure. As described above, each position of the waveform in the signal obtained from the taken image of reference unit 83 and the condition of varifocal unit 82 correspond on a one-on-one basis.

Figure 5:
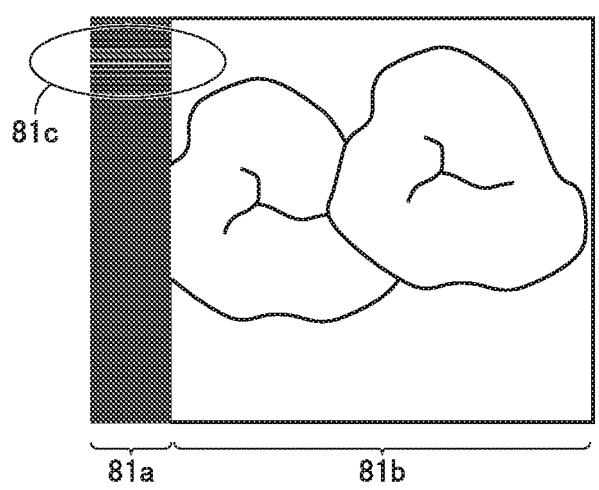
FIG. 5 is a diagram illustrating one example of images taken by the optical sensor.

According to three-dimensional scanner 100, light source unit 81 is a single light source (for example, an LED), and light from the part of light source unit 81 irradiates reference unit 83, and light reflected on reference unit 83 is detected by the part of optical sensor 85. Therefore, an image taken by optical sensor 85 contains a part of the image of the reference unit 83 in the image of object body 200. FIG. 5 is a diagram illustrating one example of images taken by optical sensor 85. The image shown in FIG. 5 shows an image of reference unit 83 in a region 81*a* on the left side of the figure, and an image of object body 200 in a region 81*b* in the remaining part of the figure. Further, a striped pattern 81*c* is shown on an upper section of the image of reference unit 83 in region 81*a*. Therefore, it is possible to specify that the image of object body 200 in FIG. 5 is an image that has been taken on the condition of varifocal unit 82 on which the focus is brought to the position of the upper section of reference unit 83 as illustrated in FIG. 4. According to three-dimensional scanner 100, it is possible to obtain the three-dimensional shape of object body 200 by combining a plurality of images of object body 200, based on the condition of varifocal unit 82 specified from the image of reference unit 83 in region 81*a*.

{Pre-Calibration of Varifocal Unit}

Figure 6:
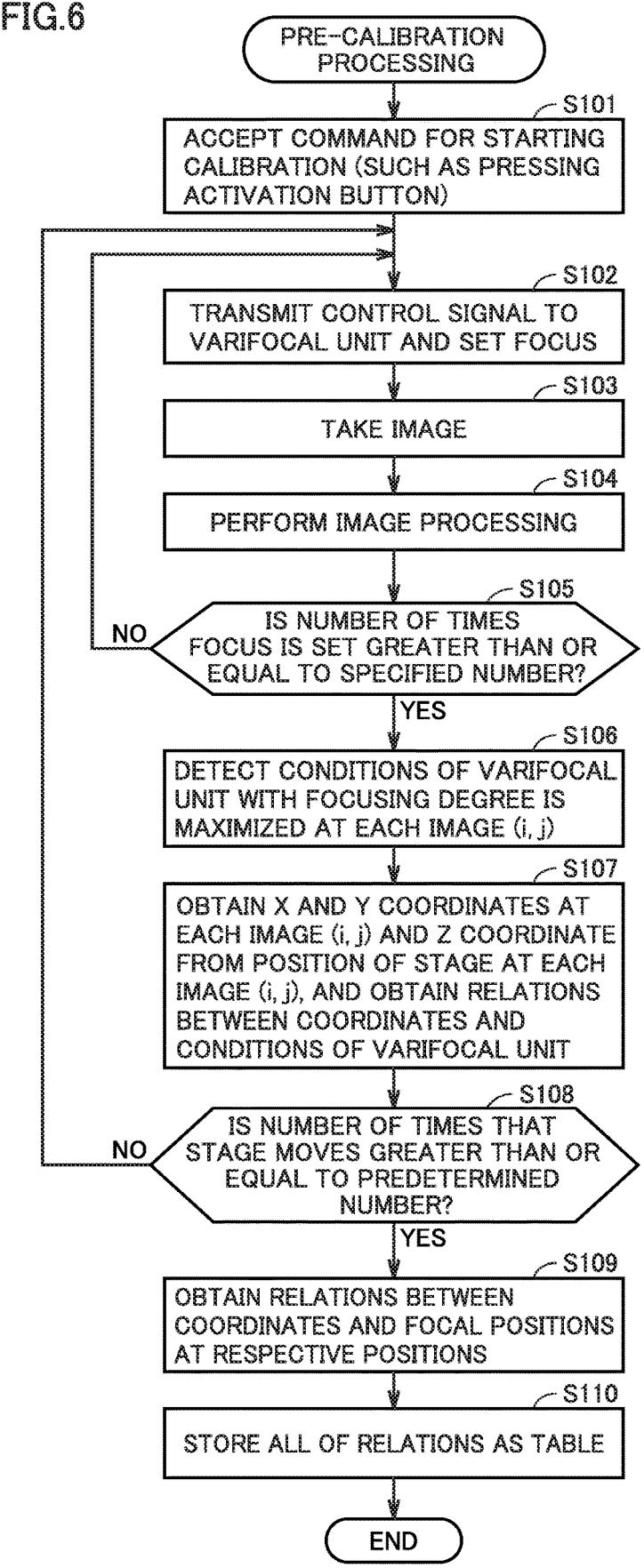
FIG. 6 is a flowchart for describing pre-calibration of the varifocal unit.

According to three-dimensional scanner 100, characteristics of varifocal unit 82 is first grasped, and therefore pre-calibration for obtaining correspondence between the focusing position for object body 200 and the focusing position for reference unit 83 is performed. Pre-calibration of varifocal unit 82 is performed, for example, at the shipment of three-dimensional scanner 100 by the manufacturer, or before the usage of three-dimensional scanner 100 by the user. Hereinafter, the pre-calibration will be described with reference to a flowchart. FIG. 6 is a flowchart for describing pre-calibration of varifocal unit 82. First, in order to perform the pre-calibration of varifocal unit 82, three-dimensional scanner 100 is fixed, and an object body having a known shape is placed on a stage that can be accurately moved with respect to three-dimensional scanner 100. Examples of the object body having a known shape include a ceramic flat plate on which a squared pattern is printed, and a ceramic plate with step processing. Further, while in the following example, a stage that is movable accurately is used as a device for pre-calibration, a jig that can correctly grasp a positional relation between three-dimensional scanner 100 and the object body (a jig having a tubular housing that can be accurately fitted to connecting section 20) may be used in place of the stage that is movable accurately.

Control unit 40 illustrated in FIG. 1 accepts a command for starting calibration (for example, such as pressing an activation button) (Step S101). Control unit 40 transmits a control signal to varifocal unit 82, and set a focus (Step S102). Varifocal unit 82 changes a focal position based on the control signal. Control unit 40 takes an image of an object body by optical sensor 85 on conditions of varifocal unit 82 that has been set (Step S103). Here, the image that has been taken includes the image of reference unit 83 and the image of the object body as described with reference to FIG. 5.

Next, control unit 40 performs image processing to the image taken in Step S103 (Step S104). Specifically, control unit 40 calculates a focusing degree (quantification on how match the image is in focus) for each pixel from the image of the object body, and calculates the condition of varifocal unit 82 (e.g., a position of waveform shown in a signal illustrated in FIGS. 4(*a*)-4(*c*)) from the image of reference unit 83. Control unit 40 determines whether or not a number of times the focus is set in Step S102 is greater than or equal to a specified number (Step S105). If the number of times the focus is set is less than the specified number (Step S105: NO), control unit 40 returns the processing to Step S102 and sets a next focus. In other words, from a minimum position to a maximum position at which setting can be performed, control unit 40 changes the condition of varifocal unit 82 at least once, and repeats image processing of images taken at corresponding focal positions (Steps S103 and S104).

If the number of times the focus is set is greater than or equal to the specified number (Step S105: YES), control unit 40 detects the condition of varifocal unit 82 with a focusing degree calculated at each image (i, j) is maximized (Step S106). In other words, control unit 40 obtains images that are in focus (all of focused images), and information of the condition of varifocal unit 82 at each time. Further, control unit 40 obtains X and Y coordinates at each image (i, j) from analysis of all of the focus images of the object body having a known shape (e.g., squared-pattern design), and a Z coordinate from a position of the stage at each image (i, j), and obtains relations between the coordinates and the condition of varifocal unit 82 respectively (Step S107). Next, control unit 40 determines whether or not a number of times the stage is moved is greater than or equal to a predetermined number (Step S108). If the number of times the stage is moved is less than the predetermined number (Step S108: NO), control unit 40 returns the processing to Step S102 and moves the stage to a next position. In other words, from a minimum position to a maximum position at which three-dimensional scanner 100 can take image, control unit 40 moves the stage at least once, and repeats image processing of images taken at corresponding positions of the stage (Steps S103 and S104). If the number of times the stage is moved is greater than or equal to the predetermined number (Step S108: YES), control unit 40 obtains relations between the coordinates and the condition of varifocal unit 82 respectively at the positions to which the stage is moved (Step S109).

Next, control unit 40 stores all of the relations obtained in Step S109 (calibration information) in a recording unit (e.g., flash memory, or the like) as a table (Step S110). Control unit 40 stores the table, and terminates the pre-calibration processing of varifocal unit 82.

Here, while control unit 40 is described to store all of the relations obtained in Step S109 (calibration information) in the recording unit as a table, all of the relations (calibration information) may not be stored as a table and may be approximated by a function, and only an expression and a coefficient of the function may be stored. Further, the pre-calibration processing may be separately performed for each of the coordinates (X, Y, and Z). For example, after the pre-calibration processing (pre-calibration for the Z coordinate) is performed using a white plate is first used as the object body, a squared-pattern plate is placed as the object body and the pre-calibration processing (pre-calibration for the X and Y coordinates) is performed.

In the above description, an example of the pre-calibration of the three-dimensional scanner using the principles of the focusing method has been described. The pre-calibration is configured roughly by three processing parts described below:

(1) obtaining a three-dimensional coordinate from an image taken by the part of optical sensor 85 of an object body having a known shape and a known traveling distance;

(2) obtaining the condition of varifocal unit 82 from an image of the reference unit taken by another part of optical sensor 85; and (3) storing correspondence between (1) and (2).

As the processing part (1) can be realized using principles of any method such as trigonometry other than the focusing method, similar pre-calibration can be applied regardless of the principles. It should be understood that this applies to the following description of measurement of the object body, regardless of the employed principles.

{Measurement of Object Body}

Figure 7:
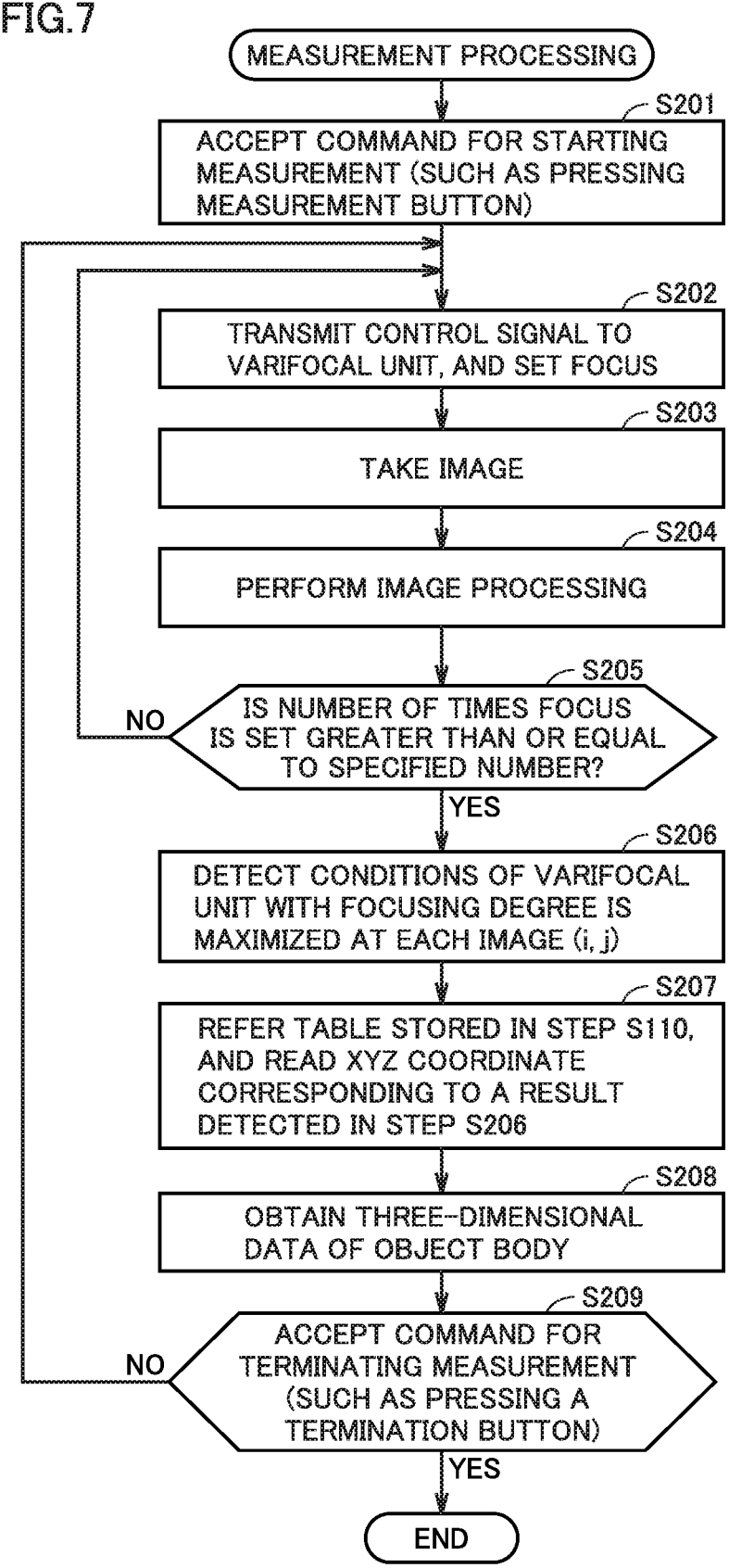
FIG. 7 is a flowchart describing measurement of an object body by the three-dimensional scanner according to Embodiment 1 of the present invention.

Three-dimensional scanner 100 measures the object body using the relations obtained by the pre-calibration processing of varifocal unit 82. Hereinafter, the measurement of the object body will be described with reference to a flowchart. FIG. 7 is a flowchart describing measurement of an object body by the three-dimensional scanner according to Embodiment 1 of the present invention.

Control unit 40 illustrated in FIG. 1 accepts a command for starting measurement of object body 200 (for example, such as pressing a measurement button) (Step S201). Control unit 40 transmits a control signal to varifocal unit 82, and set a focus (Step S202). Varifocal unit 82 changes a focal position based on the control signal. Control unit 40 takes an image of an object body by optical sensor 85 on conditions of varifocal unit 82 that has been set (Step S203).

Next, control unit 40 performs image processing to the image taken in Step S203 (Step S204). Specifically, control unit 40 determines a focusing degree for each pixel from the image of the object body, and calculates the conditions of varifocal unit 82 from the image of reference unit 83. Control unit 40 determines whether or not the number of times the focus is set in Step S202 is greater than or equal to a specified number (Step S205). If the number of times the focus is set is less than the specified number (Step S205: NO), control unit 40 returns the processing to Step S202 and sets a next focus. In other words, from a minimum position to a maximum position at which setting can be performed, control unit 40 changes the condition of varifocal unit 82 at least once, and repeats image processing of images taken at corresponding focal positions (Steps S203 and S204).

If the number of times the focus is set is greater than or equal to the specified number (Step S205: YES), control unit 40 detects the condition of varifocal unit 82 with a focusing degree calculated at each image (i, j) is maximized (Step S206). In other words, control unit 40 obtains images that are in focus, and information of the condition of varifocal unit 82 at each time. Further, control unit 40 refers to the table stored in Step S110, and reads a three-dimensional coordinate (X, Y, and Z coordinates) corresponding to a result detected for each pixel in Step S206 (the condition of varifocal unit 82) (Step S207). At this time, if the condition of varifocal unit 82 stored in the table does not match the condition of varifocal unit 82 detected in Step S206, it is possible to perform interpolation processing using values close to the stored conditions of varifocal unit 82 in the table. Further, if a value close to the condition of varifocal unit 82 detected in Step S206 is not present in the table, it is determined that a measurement error occurs and it is possible to perform outlier processing in which a coordinate is not generated. Based on Steps S202 to S208, control unit 40 obtains three-dimensional coordinates for all of the coordinates, and obtains three-dimensional data of object body 200 (Step S208).

Next, control unit 40 accepts a command for terminating the measurement of object body 200 (for example, such as pressing a termination button) (Step S209). If a command for terminating the measurement is not accepted (Step S209: NO), control unit 40 returns the processing to Step S202 in order to continue the measurement processing, and repeats the processing for obtaining the three-dimensional data (Steps S202 to S208). By repeating the above steps, it is possible to perform successive three-dimensional measurement like a video. On the other hand, if a command for terminating the measurement is accepted (Step S209: YES), control unit 40 terminates the measurement processing.

As described above, three-dimensional scanner 100 according to Embodiment 1 of the present invention includes: light source unit 81, optical sensor 85 for detecting the light from light source unit 81 that has been reflected on object body 200; and reference unit 83 for being irradiated with a part of the light from light source unit 81. Three-dimensional scanner 100 further includes: varifocal unit 82 capable of changing the focal position, varifocal unit being a unit through which both of the light from light source unit 81 to optical sensor 85 via object body 200 and the light from light source unit 81 to optical sensor 85 via reference unit 83 travel at least once; and the light path length adjustment unit for adjusting the length of the light path from object body 200 to optical sensor 85 and the length of the light path from reference unit 83 to optical sensor 85. Further, three-dimensional scanner 100 causes control unit 40 to determine the condition of varifocal unit 82 based on the light detected by the part of optical sensor 85 (the light reflected on reference unit 83), and to calculate the shape information of object body 200 from the light detected by optical sensor 85 using the information of the determined condition of varifocal unit 82. Therefore, three-dimensional scanner 100 is able to correctly grasp the condition of varifocal unit 82, and to obtain an accurate three-dimensional shape. In addition, as three-dimensional scanner 100 does not require a configuration in which the lens of varifocal unit 82 is provided with a gauge and optical detection is performed, a size of handpiece 80 itself can be reduced.

Further, reference unit 83 is provided within the housing of handpiece 80, it is possible to perform pre-calibration processing without probe 10. Moreover, optical sensor 85 is configured by a single optical sensor, and the part of optical sensor 85 detects the light reflected on reference unit 83, and the remaining part of optical sensor 85 detects the light reflected on object body 200. Therefore, it is possible to reduce a number of components of three-dimensional scanner 100. It should be appreciated that optical sensor 85 may be configured by a plurality of optical sensors, and one of the optical sensors is used to detect the light reflected on reference unit 83, and the other of the optical sensors is used to detect the light reflected on object body 200.

Modified Example 1

According to three-dimensional scanner 100 illustrated in FIG. 2, the light from light source unit 81 to optical sensor 85 via object body 200 travels through varifocal unit 82 two times, and the light from light source unit 81 to optical sensor 85 via reference unit 83 also travels through varifocal unit 82 two times. However, it is sufficient if the light from light source unit 81 to optical sensor 85 via object body 200 and the light from light source unit 81 to optical sensor 85 via reference unit 83 travel through varifocal unit 82 at least once. In order to provide a configuration in which both of the light from light source unit 81 to optical sensor 85 via object body 200 and the light from light source unit 81 to optical sensor 85 via reference unit 83 travel through varifocal unit 82 once, varifocal unit 82 may be provided closer to light source unit 81 or optical sensor 85 than a beam splitter that is not illustrated in FIG. 2.

Further, it is possible to provide a configuration in which only the light from light source unit 81 to optical sensor 85 via reference unit 83 travels through varifocal unit 82 once, or only the light from light source unit 81 to optical sensor 85 via object body 200 travels through varifocal unit 82 once. FIGS. 8(*a*)-8(*b*) are schematic diagrams illustrating a configuration of an optical system within a handpiece according to a modified example of Embodiment 1 of the present invention. Here, in the configurations illustrated in FIG. 8(*a*)-8(*b*), components that are the same as those in the configuration illustrated in FIG. 2 are indicated by the same reference numbers and not described in detail. The configuration illustrated in FIG. 8(*a*) is such that only the light from light source unit 81 to optical sensor 85 via reference unit 83 travels through varifocal unit 82 once, and the light from light source unit 81 is split using a light guide 91 (for example, such as an optical fiber) to directly irradiate reference unit 83. In other words, light output from a light guide 92 after being split irradiates reference unit 83 without traveling through varifocal unit 82. The light irradiating reference unit 83 is reflected on reference unit 83, travels through a collimate lens 93, varifocal unit 82, and a beam splitter 88, and is detected by the part of optical sensor 85. On the other hand, light output from the other light guide after being split by light guide 91 travels through a collimate lens 86, a pattern generating element 87, beam splitter 88, and varifocal unit 82, and irradiates the object body. Here, the configuration illustrated in FIG. 8(*a*) is mere example, and a part of the components in this configuration may be replaced by an equivalent optical element.

Figure 8A:
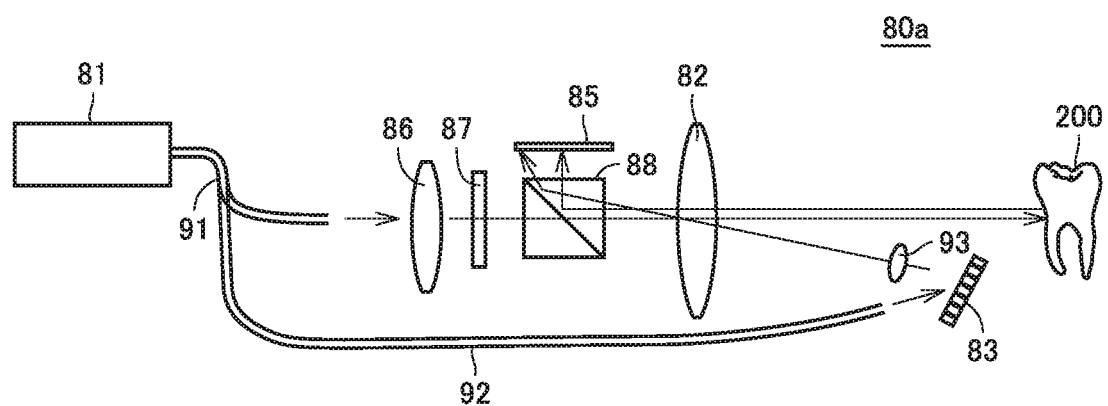
FIGS. 8(a)-8(b) are schematic diagrams illustrating a configuration of an optical system within a handpiece according to a modified example of Embodiment 1 of the present invention.
Figure 8B:
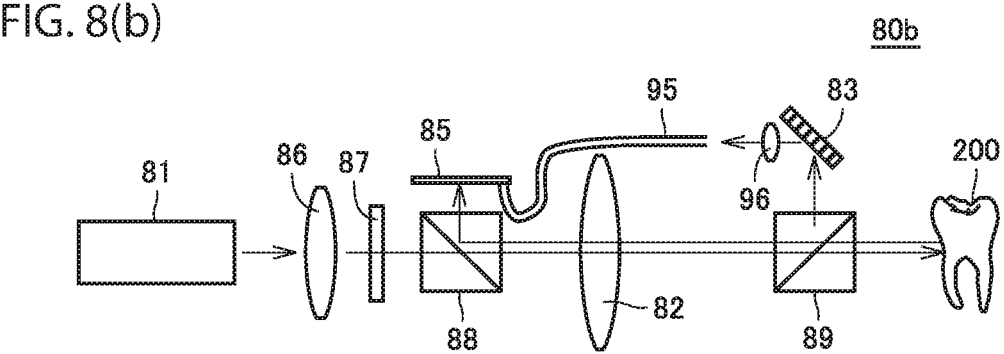

The configuration illustrated in FIG. 8(b) is such that only the light from light source unit 81 to optical sensor 85 via object body 200 travels through varifocal unit 82 once, and the light reflected on reference unit 83 is directly guided to optical sensor 85 using a light guide 95 (for example, such as an optical fiber). In other words, a part of the light from light source unit 81 that has traveled through varifocal unit 82 once irradiates reference unit 83, and the light reflected on reference unit 83 is collected by an imaging lens 96 and guided to optical sensor 85 by light guide 95. On the other hand, the light reflected on object body 200 travels through beam splitter 88, varifocal unit 82, and beam splitter 88, and is detected by optical sensor 85. Here, the configuration illustrated in FIG. 8(b) is mere example, and a part of the components in this configuration may be replaced by an equivalent optical element. Further, while not described in the above configuration, it is possible to provide a configuration having a light path along which light travels through varifocal unit 82 by a number of times greater than or equal to three.

Modified Example 2

While light source unit 81 is described to be a single light source (for example, an LED, and a laser element), light source unit is not limited to such a configuration. Light source unit 81 may be configured by combining a plurality of light sources. In other words, light source unit 81 may be configured by a plurality of LEDs or laser elements arranged on a substrate. Further, light source unit 81 irradiates reference unit 83 with a part of the light, and irradiates object body 200 with the other part of the light. Therefore, light source unit 81 may be configured by a light source unit A that emits light irradiating object body 200, and a light source unit B that emits light irradiating reference unit 83. Moreover, light source unit A and light source unit B are not required to be disposed close to each other, and light source unit A and light source unit B may be disposed at distant positions. Here, according to three-dimensional scanner 100, it is possible to employ a configuration in which the light from light source unit 81 is guided to reference unit 83 and object body 200 using a light guide such as an optical fiber.

Embodiment 2

Embodiment 1 describes three-dimensional scanner 100 having a configuration, as illustrated in FIG. 2, in which reference unit 83 is provided within the housing of handpiece 80. However, a three-dimensional scanner according to Embodiment 2 is provided with a reference unit within a probe detachable from an optical measurement unit, in place of the reference unit within the housing of the handpiece. Hereinafter, a three-dimensional scanner having a reference unit within a probe will be described.

{Configuration of Probe}

Figure 9:
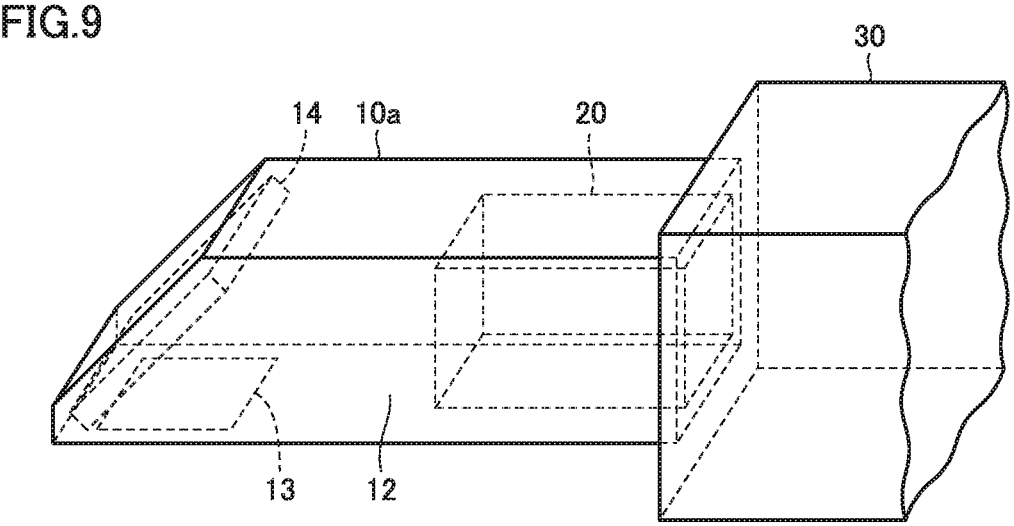
FIG. 9 is a schematic diagram illustrating a configuration of a probe according to Embodiment 2 of the present invention.

First, a configuration of the probe will be described in detail. FIG. 9 is a schematic diagram illustrating a configuration of a probe 10a according to Embodiment 2 of the present invention. Here, in FIG. 9, components that are the same as those in the configuration illustrated in FIG. 1 and FIG. 2 are indicated by the same reference numbers and not described in detail. Probe 10a includes a housing 12 having an opening for connection with connecting section 20, a measurement window 13 (lighting window unit) provided for housing 12 on the other side of the opening, and a mirror 14 (reflection unit) for reflecting light received through measurement window 13 to optical measurement unit 30. The opening of probe 10a is an insertion portion through which connecting section 20 is inserted. With this, even if an external force is applied to housing 12, probe 10a does not be easily separated from connecting section 20. Further, as illustrated in FIG. 9, an end portion of probe 10a is in contact with optical measurement unit 30. With this, even if probe 10a is pressed toward a direction of optical measurement unit 30, probe 10a does not move toward optical measurement unit 30 anymore.

Mirror 14 is an optical element for changing directions of the light from light source unit 81 and the light reflected on object body 200, and includes a reference unit at a part thereof. Here, in order to realize the configuration in which "mirror 14 includes the reference unit at a part thereof", the reference unit may be provided by forming a design pattern or the like on a part of a surface of mirror 14, or the reference unit may be provided by applying a separate member having a design pattern on a part of a surface of mirror 14. Further, mirror 14 may be configured by combining an optical element for reflecting light and a reference unit as a separate member.

{Configuration of Optical System}

Figure 10:
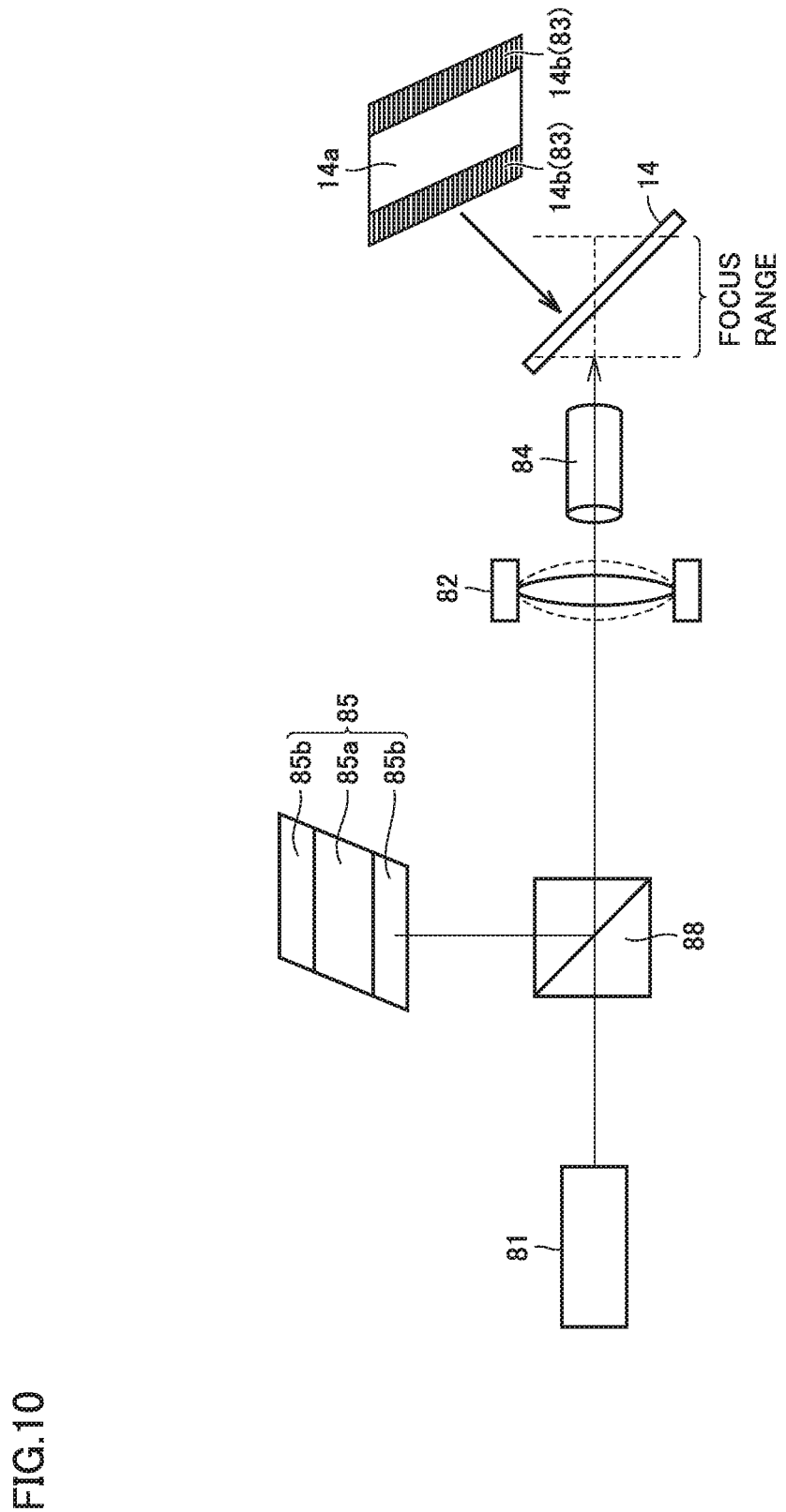
FIG. 10 is a schematic diagram illustrating a configuration of an optical system of a three-dimensional scanner according to Embodiment 2 of the present invention.

Next, a configuration of an optical system of the three-dimensional scanner according to Embodiment 2 will be described more in detail. FIG. 10 is a schematic diagram illustrating a configuration of an optical system of a three-dimensional scanner according to Embodiment 2 of the present invention. Here, in FIG. 10, components that are the same as those in the configuration illustrated in FIG. 1 and FIG. 2 are indicated by the same reference numbers and not described in detail. First, the three-dimensional scanner according to Embodiment 2 includes light source unit 81, varifocal unit 82, reference unit 83, light path length adjustment unit 84, optical sensor 85, and beam splitter 88. Here, FIG. 10 only shows a light path from the part of light source unit 81 to the part of optical sensor 85 through reference unit 83. A light path from light source unit 81 to optical sensor 85 through object body 200 is the same as the light path described in Embodiment 1, and not described in detail.

Light from light source unit 81 travels through beam splitter 88, varifocal unit 82, and light path length adjustment unit 84, and irradiates mirror 14. With mirror 14, striped patterns 14b formed on both sides serve as reference unit 83, and the remaining part serves as a light reflector 14a. A part of the light irradiating mirror 14 is reflected on reference unit 83 on which striped patterns 14b are formed. The light reflected on reference unit 83 travels through light path length adjustment unit 84, varifocal unit 82, and beam splitter 88, and is detected by optical sensor 85. Optical sensor 85 detects the light from object body 200 at a central portion 85a, and detects the light from reference unit 83 at portions 85b on the both sides. Similarly to the example shown in FIGS. 4(a)-4(c), as a surface having the striped pattern is disposed so as to be inclined with respect to a light axis of light sensor, a striped design pattern appears in an image at a position corresponding to the condition of varifocal unit 82 on a one-on-one basis.

As described above, as reference unit 83 is provided for probe 10a detachable from the opening of three-dimensional scanner, and no reference unit is required within the housing of the handpiece, a size of the housing can be reduced. Further, as reference unit 83 is provided for a part of mirror 14 as an optical element, a number of the components can be reduced as compared to a case in which a reference unit is prepared as a separate member. Here, reference unit 83 is not limited to the example illustrated in FIG. 10 in which reference unit 83 is provided on the both sides of mirror 14, and may be provided only on one side of mirror 14.

Modified Example

Figure 11:
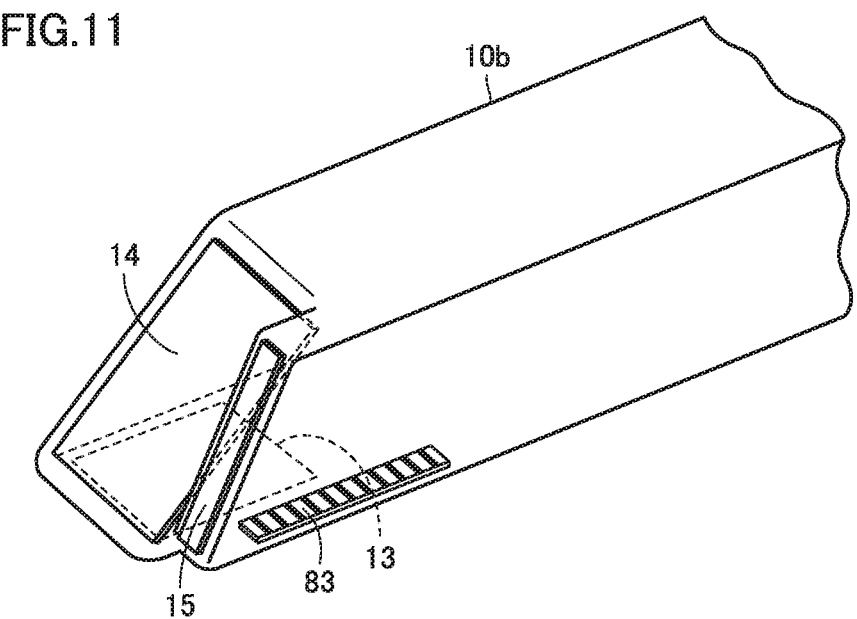
FIG. 11 is a schematic diagram illustrating a configuration of a probe according to a modified example of Embodiment 2 of the present invention.

Probe 10a illustrated in FIG. 9 and FIG. 10 has the configuration in which reference unit 83 is provided for the part of mirror 14. However, the reference unit may be provided for a different position within the probe, instead of the part of mirror 14. FIG. 11 is a schematic diagram illustrating a configuration of a probe according to a modified example of Embodiment 2 of the present invention. A probe 10b illustrated in FIG. 11 includes reference unit 83 near measurement window 13, and an offset mirror 15 for reflecting the light from reference unit 83 next to mirror 14. Offset mirror 15 also serves as a light path length adjustment unit for adjusting a length of the light path from the part of light source unit 81 to the part of optical sensor 85 through reference unit 83. Further, in order to cause offset mirror 15 to serve as the light path length adjustment unit, and in order to provide the light axis of the light sensor inclined with respect to reference unit 83, an angle of mirror 14 with respect to the surface in which measurement window 13 is formed and an angle of offset mirror 15 with respect to this surface are different.

Embodiment 3

In three-dimensional scanner 100 according to Embodiment 1, as illustrated in FIG. 2, the light from the light source unit 1 irradiates reference unit 83. While the light irradiating reference unit 83 is reflected on reference unit 83, there is a case in which a part of the light irregularly reflects and reaches the optical sensor as stray light. The stray light is a cause of a decreased accuracy of the three-dimensional measurement. A three-dimensional scanner according to Embodiment 3 has a configuration for suppressing such stray light.

Figure 12:
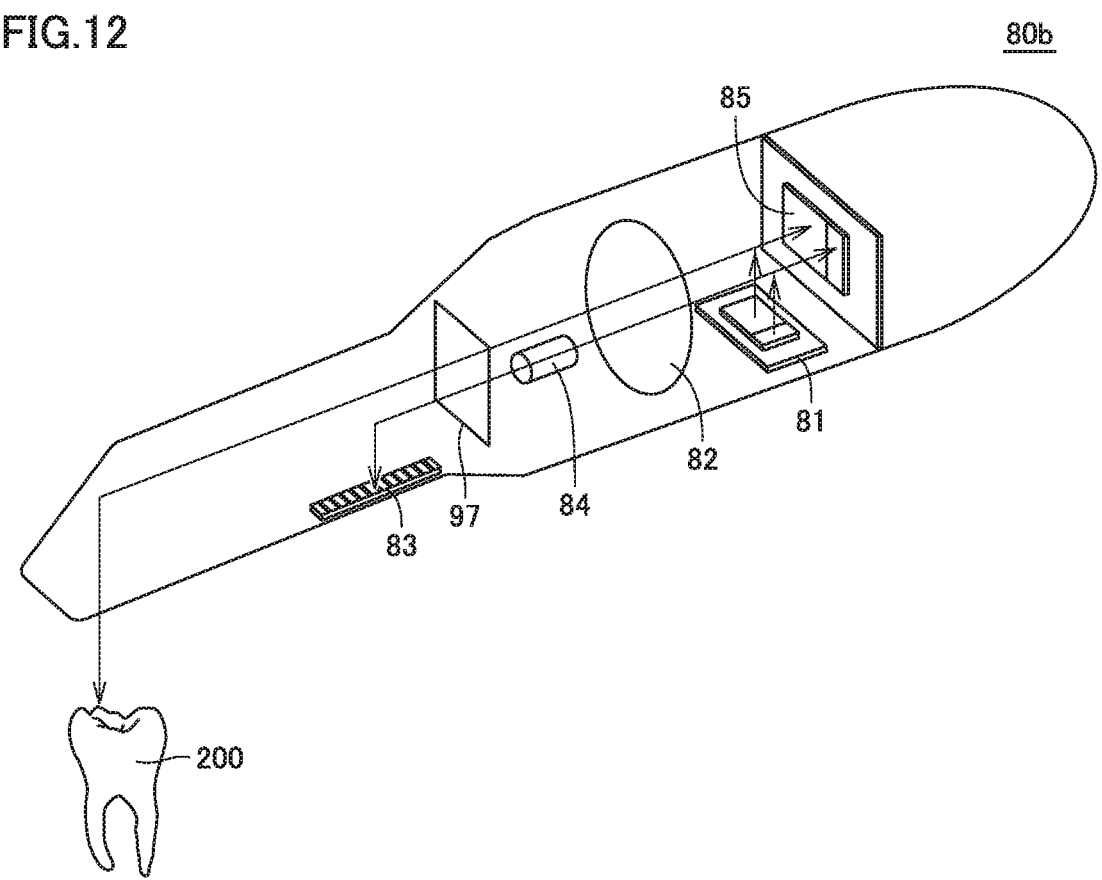
FIG. 12 is a schematic diagram illustrating a configuration of an optical system within a handpiece according to Embodiment 3 of the present invention.

FIG. 12 is a schematic diagram illustrating a configuration of an optical system within a handpiece according to Embodiment 3 of the present invention. Here, in FIG. 12, components that are the same as those in the configuration illustrated in FIG. 1 and FIG. 2 are indicated by the same reference numbers and not described in detail. First, a handpiece 80b according to Embodiment 3 includes light source unit 81, varifocal unit 82, reference unit 83, light path length adjustment unit 84, and optical sensor 85. Further, handpiece 80b includes a diaphragm unit 97 for adjusting light to optical sensor 85 at any position along the light path from reference unit 83 to optical sensor 85. Diaphragm unit 97 cuts the light that irregularly reflects on reference unit 83 as stray light so that the light does not be detected by optical sensor 85. Diaphragm unit 97 may have any diaphragm mechanism as long as it is possible to cut light.

As described above, by further providing diaphragm unit 97 for adjusting light to optical sensor 85, it is possible to cut the light that irregularly reflects on reference unit 83 as stray light, and to improve accuracy of the three-dimensional measurement. Here, FIG. 12 shows the configuration in which diaphragm unit 97 is provided for an optical system within the handpiece having reference unit 83 within the housing. However, a diaphragm unit may also be provided for an optical system within a handpiece having a reference unit within a probe.

Embodiment 4

According to the probe according to Embodiment 2, reference unit 83 is provided for the part of mirror 14. A probe according to Embodiment 4 has a configuration in which a retardation plate is provided for a surface of a reference unit provided for a part of a mirror.

Figure 13:
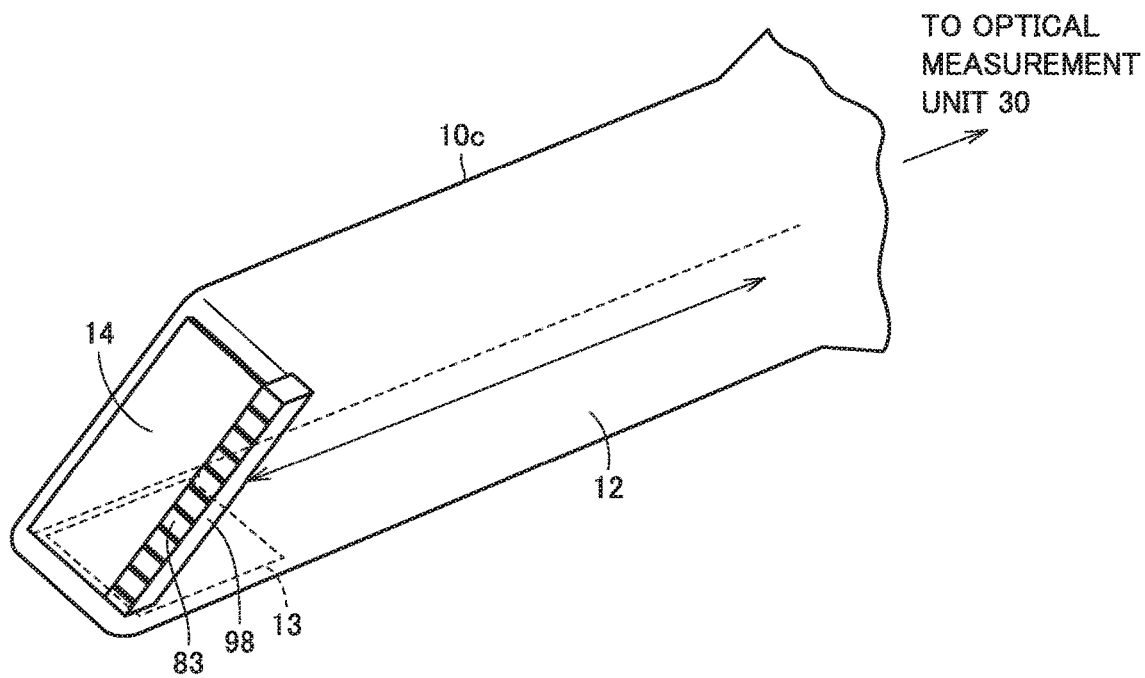
FIG. 13 is a schematic diagram illustrating a configuration of a probe according to Embodiment 4 of the present invention.

FIG. 13 is a schematic diagram illustrating a configuration of a probe 10c according to Embodiment 4 of the present invention. Here, in FIG. 13, components that are the same as those in the configuration illustrated in FIG. 9 and FIG. 11 are indicated by the same reference numbers and not described in detail. Probe 10c includes a housing 12 having an opening for connection with a connecting section of the optical measurement unit, a measurement window 13 (lighting window unit) provided for housing 12 on the other side of the opening, and a mirror 14 (reflection unit) for reflecting light received through measurement window 13 to optical measurement unit 30.

Mirror 14 includes reference unit 83 at a part thereof. Here, while reference unit 83 is provided only on one side of mirror 14 as illustrated in FIG. 13, reference unit 83 may be provided on both sides of mirror 14. Further, a quarter wavelength plate 98 as a retardation plate is provided for the surface of reference unit 83. By providing quarter wavelength plate 98 for the surface of reference unit 83, it is possible to efficiently detect the light reflected on reference unit 83 by optical sensor 85. Here, a quarter wavelength plate is a retardation plate having a function for producing a ¼ wavelength phase difference in a specific polarization component contained in an incident light beam. With this, polarization states of incident light and reflection light may be operated. This is effective, for example, to a case in which beam splitter 88 is configured by a polarization beam splitter, and reference unit 83 is configured by a translucent resin material or the like, and it is possible to emphasize contrast of a pattern projected onto the surface of reference unit 83 by employing quarter wavelength plate 98. Specifically, utilizing a difference between the polarization states of a component reflected near the surface (a component having favorable contrast of the pattern) and a component diffusely reflected within a translucent body (a component reducing contrast of the pattern) out of the reflection light from reference unit 83, only the former component is selectively guided to optical sensor 85 with low loss. With this, it is possible to improve accuracy of grasping of the condition of the varifocal unit by analyzing a taken image of reference unit 83. The retardation plate provided for the surface of reference unit 83 is not limited to quarter wavelength plate 98, and a retardation plate of an appropriate type may be selected depending on the optical design.

As described above, as reference unit 83 has a retardation plate on the surface to be irradiated with light, use efficiency of the light reflected on reference unit 83 is improved. Here, FIG. 13 shows the configuration in which the retardation plate is provided for the surface of reference unit 83 provided for the part of mirror 14. However, a retardation plate may be provided for a surface of a reference unit provided within the probe, or for a surface of a reference unit provided within the housing.

Embodiment 5

Embodiment 1 describes three-dimensional scanner 100 having a configuration in which a wavelength of light irradiating object body 200 and a wavelength of light irradiating reference unit 83 are the same. However, Embodiment 5 describes a three-dimensional scanner having a configuration in which a wavelength of light irradiating an object body and a wavelength of light irradiating a reference unit are different.

Figure 14:
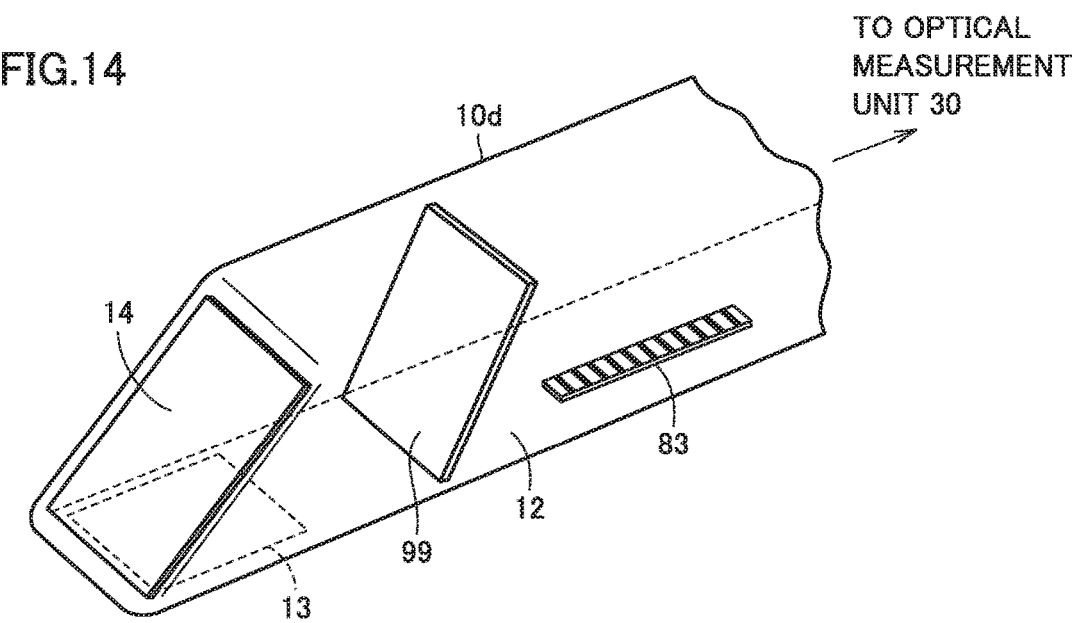
FIG. 14 is a schematic diagram illustrating a configuration of a probe according to Embodiment 5 of the present invention.

FIG. 14 is a schematic diagram illustrating a configuration of a probe 10d according to Embodiment 5 of the present invention. Here, in FIG. 14, components that are the same as those in the configuration illustrated in FIG. 9 and FIG. 11 are indicated by the same reference numbers and not described in detail. Probe 10d includes housing 12 having an opening for connection with a connecting section of optical measurement unit 30, measurement window 13 (lighting window unit) provided for housing 12 on the other side of the opening, mirror 14 (reflection unit) for reflecting light received through measurement window 13 to optical measurement unit 3, a dichroic mirror 99 disposed on a side closer to optical measurement unit 30 than measurement window 13, and reference unit 83 disposed on a side closer to optical measurement unit 30 than dichroic mirror 99.

Figure 15A:
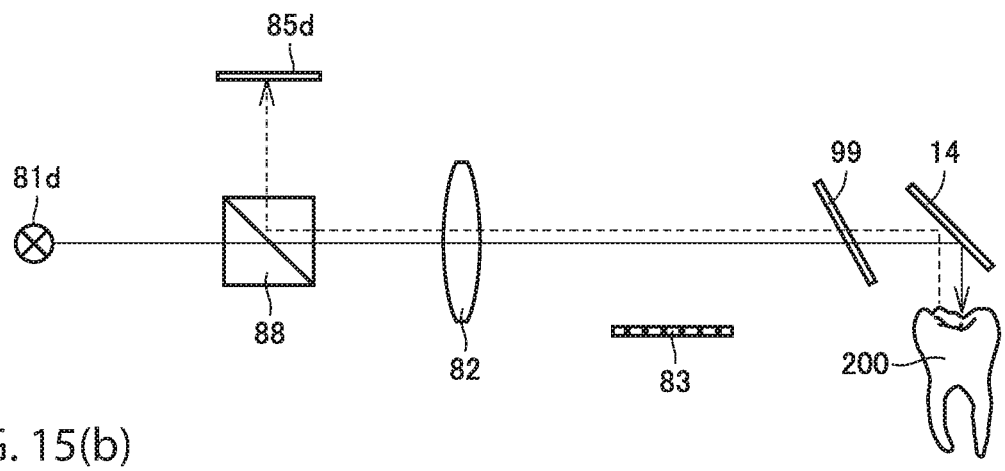
FIGS. 15(a)-15(b) are schematic diagrams illustrating a configuration of an optical system within a handpiece according to Embodiment 5 of the present invention.
Figure 15B:
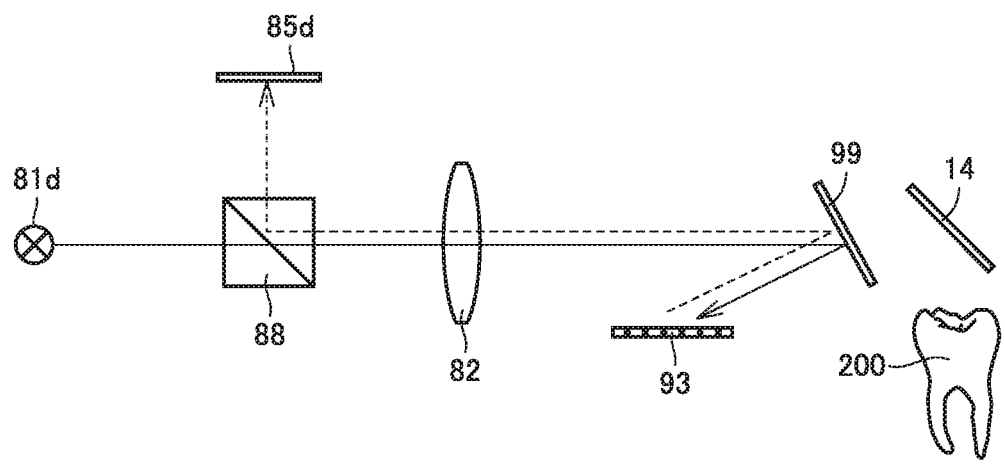

As one example of dichroic mirror 99, an optical element that transmits visible light and reflects infrared light (IR) is used here. In other words, the three-dimensional scanner according to Embodiment 5 uses visible light as the light irradiating object body 200, and infrared light as the light irradiating reference unit 83. FIGS. 15(a)-15(b) are schematic diagrams illustrating a configuration of an optical system within a handpiece according to Embodiment 5 of the present invention. In the configurations illustrated in FIGS. 15(a)-15(b), components that are the same as those in the configuration illustrated in FIG. 2 are indicated by the same reference numbers and not described in detail. A light path shown in FIG. 15(a) is a light path from a light source unit 81d to optical sensor 85d via object body 200. A light path shown in FIG. 15(b) is a light path from light source unit 81d to an optical sensor 85d via reference unit 83.

First, light source unit 81d is a light source configured to emit visible light and infrared light. Here, light source unit 81d may be, for example, configured by an LED or a laser element for emitting visible light and an LED or a laser element for emitting infrared light, the LEDs being arranged on a substrate, or by a single LED for emitting broadband light including a spectrum from visible light to infrared light. Here, light source unit 81d may be configured separately by a light source unit C for emitting visible light and a light source unit D for emitting infrared light.

With the light path shown in FIG. 15(a), visible light emitted from light source unit 81d travels through beam splitter 88, varifocal unit 82, and mirror 14, and irradiates object body 200. Light reflected on object body 200 travels inversely through mirror 14, varifocal unit 82, and beam splitter 88, and is detected by optical sensor 85. On the other hand, with the light path shown in FIG. 15(b), infrared light emitted from light source unit 81d travels through beam splitter 88, varifocal unit 82, and dichroic mirror 99, and irradiates reference unit 83. Light reflected on reference unit 83 travels inversely through dichroic mirror 99, varifocal unit 82, and beam splitter 88, and is detected by optical sensor 85d.

Figure 16A:
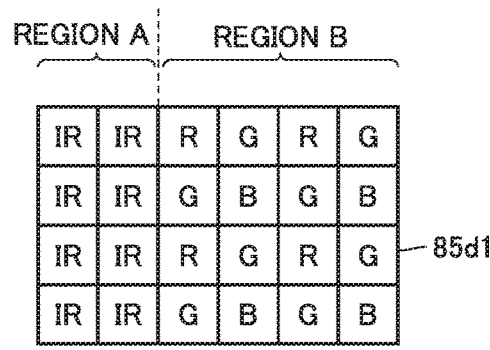
FIGS. 16(a)-16(c) are schematic diagrams illustrating a configuration of an optical sensor according to Embodiment 5 of the present invention.
Figure 16B:
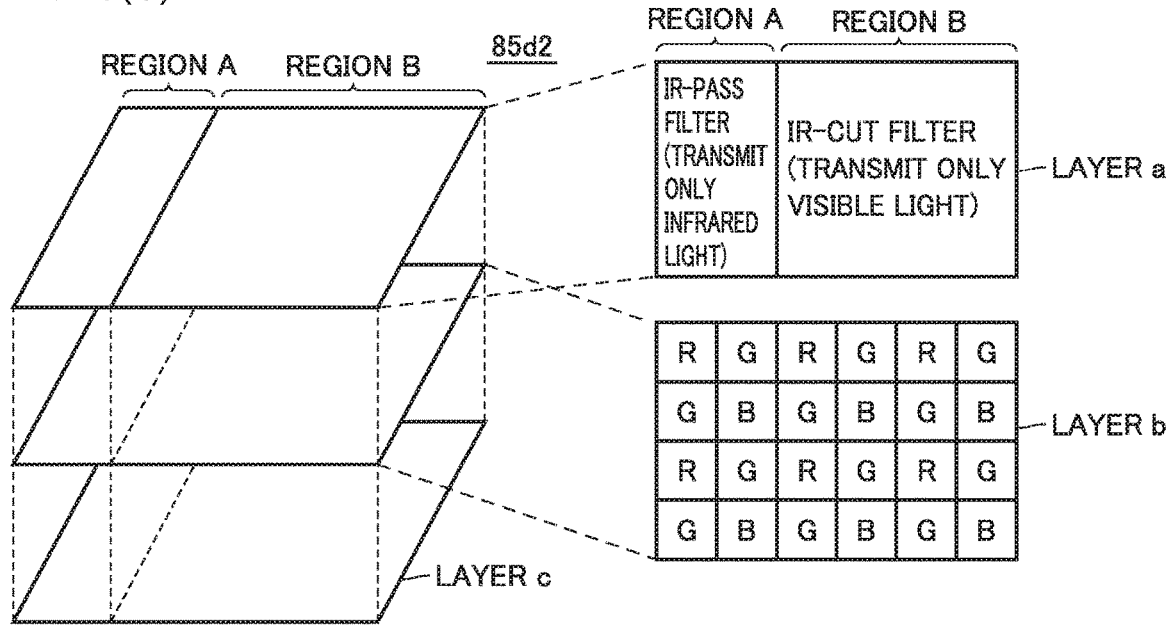
Figure 16C:
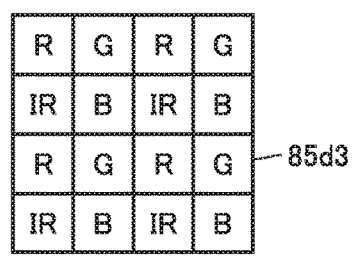

Optical sensor 85d is able to detect visible light as well as infrared light. A specific configuration of optical sensor 85d will be described with reference to the drawings. FIGS. 16(a)-16(c) are schematic diagrams illustrating a configuration of an optical sensor according to Embodiment 5 of the present invention. An optical sensor 85d1 illustrated in FIG. 16(a) has a single-layer structure, and a region in which elements for detecting infrared light are arranged and a region in which elements for detecting visible light are arranged are disposed on a plane surface. In particular, in optical sensor 85d1, the elements for detecting infrared light are arranged in a region A, and the elements for detecting visible light are arranged in a region B. It should be noted that reference signs IR, R, G, and B in the figure indicate regions with high sensitivity/transmissivity to infrared light, red light, green light, and blue light, respectively.

An optical sensor 85d2 illustrated in FIG. 16(b) has a multi-layer structure, and a layer a is provided with a filter selectively transmitting visible light and infrared light, a layer b is provided with a color filter, and a layer c is provided with a monochrome light sensor. Optical sensor 85d2 also detects infrared light in region A, and visible light in region B. Therefore, for layer a, a filter only transmitting infrared light (IR-pass filter) is provided for region A, and a filter only transmitting visible light (IR-cut filter) is provided for region B. Here, if an image to be obtained by three-dimensional scanner is a monochrome image, the color filter for layer b is not necessary, or may be a monochrome filter.

While optical sensors 85d1 and 85d2 are configured such that the region for detecting infrared light and the region for detecting visible light are separate, an optical sensor 85d3 illustrated in FIG. 16(c) has a configuration in which infrared light and visible light are detected without separating regions. Optical sensor 85d3 has a single layer structure, and elements for detecting infrared light and elements for detecting visible light are arranged in sequence. In particular, in optical sensor 85d3, RGB elements for detecting visible light of respective colors and the elements for detecting infrared light are arranged in sequence. It should be understood that optical sensor 85d may be configured such that more than one area in which the elements for detecting visible light are disposed, and more than one area in which the elements for detecting infrared light are disposed are arranged. Further, similarly to optical sensor 85d2, optical sensor 85d3 may have a multi-layer structure in place of the single layer structure. As compared to optical sensor 85d1, 85d2 with the configuration in which an image of the reference unit is detected using a region on the side of the optical sensor, optical sensor 85d3 is able to detect infrared light at the center portion of the sensor, and therefore has an advantage that optical sensor 85d3 is less susceptible to aberration of the lens and the like.

As described above, according to the three-dimensional scanner of Embodiment 5, as the wavelength of the light which is emitted from light source unit 81d and which irradiates reference unit 83 (infrared light) and the wavelength of the light which is emitted from light source unit 81d and which irradiates object body 200 (visible light) are different, even if irregularly-reflected light on reference unit 83 interferes an image of object body 200 as stray light, for example, the stray light does not be present in a taken image of object body 200 by the color filter. Therefore, it is possible to grasp the condition of varifocal unit 82 without giving any influence to the measurement of object body 200.

While the three-dimensional scanner according to Embodiment 5 uses infrared light and visible light so that the wavelength of the light which is emitted from light source unit 81d and which irradiates reference unit 83 and the wavelength of the light which is emitted from light source unit 81d and which irradiates object body 200 are different, a combinations of other wavelengths may be employed, and for example, ultraviolet light (UV) and visible light may be used.

Modified Example

The three-dimensional scanner according to Embodiments 1 to 5 of the present invention is descried to have a striped pattern formed on the surface of reference unit 83. However, the pattern formed on the surface of reference unit 83 is not limited to the striped (striped) pattern, and may be a grid pattern or a dotted pattern. Further, the surface may not be inclined with respect to the light axis of the optical sensor. For example, in a case in which a dotted pattern is formed on the surface of reference unit 83, it is possible to grasp the condition of varifocal unit 82 based on a diameter of a dot out of focus (a diameter of a circle of confusion). Here, the pattern formed on the surface of reference unit 83 may be any pattern as long as visibility of the pattern changes depending on the change of the condition of varifocal unit 82, and a degree of the change may be quantified. Further, reference unit 83 may be provided with the pattern by directly printing a pattern to the surface, or by applying a pattern printed on a separate member to the surface. Examples of reference unit 83 include a striped design pattern formed on a base material such as paper, plastic, metal, ceramic, and glass by screen printing, laser marking, vapor deposition, sputtering, and alternate stacking of materials of different colors by a 3D printer. Further, a design pattern may be formed by such as shape processing for concavity and convexity in place of changing surface colors, or a combination of both.

Moreover, as illustrated in FIGS. 8(a)-8(b), by providing pattern generating element 87 along the light path, it is possible to provide a predetermined pattern for the light irradiating reference unit 83. It is possible to project a predetermined pattern onto the surface of reference unit 83 by providing the predetermined pattern for the light irradiating reference unit 83, without forming a pattern on the surface of reference unit 83. It should be appreciated that a combination of reference unit 83 having a pattern on its surface and the light having a predetermined pattern may also be employed.

The three-dimensional scanner according to Embodiment 1 of the present invention is described to have the configuration in which reference unit 83 is provided on the side of the housing of the handpiece, and the three-dimensional scanner according to Embodiment 2 of the present invention is described to have the configuration in which reference unit 83 is provided on the side of the probe. Further, the probe according to Embodiment 2 of the present invention is provided with mirror 14 in addition to reference unit 83. However, the present invention is not limited to such configurations, and a configuration in which the probe is only provided with reference unit 83, and a configuration in which mirror 14 is provided on the side of the housing of the handpiece in addition to reference unit 83 may also be employed. Here, in a case in which reference unit 83 and mirror 14 are provided on the side of the housing of the handpiece, the probe is used only as a cover. Further, while the three-dimensional scanner having the probe detachable from the housing of the handpiece is described, as long as a structure with which aseptic of the handpiece as a whole can be performed is provided, the configuration described with reference to Embodiments 1 to 5 may be applied to a three-dimensional scanner having no probe. According to the three-dimensional scanner of Embodiment 1 of the present invention, it is described that light path length adjustment unit 84 is provided along the light path on the side of reference unit 83 in order to adjust the length of the light path from light source unit 81 to optical sensor 85 through object body 200 and the length of the light path from the part of light source unit 81 to the part of optical sensor 85 through reference unit 83. However, as long as it is possible to relatively adjust the length of the light path from light source unit 81 to optical sensor 85 through object body 200 and the length of the light path from the part of light source unit 81 to the part of optical sensor 85 through reference unit 83, the light path length adjustment unit may be provided either of the light paths. It should be appreciated that the light path length adjustment unit may be provided along both of the light path for reference unit 83 and the light path for object body 200. Further, forming an image of reference unit 83 or object body 200 at a predetermined position along the light path using a relay lens and an image guide may provide a situation that can be considered equivalent to a situation in which reference unit 83 or object body 200 is actually placed at the position at which the image is formed. Therefore, light path length adjustment unit 84 may be configured to specify a length of the light path for a position at which an image is formed, and to adjust the length of the light path, instead of a position at which reference unit 83 or object body 200 is actually placed.

Further, an object of the three-dimensional scanner according to Embodiments 1 to 5 of the present invention is not limited to a tooth and gum in the mouth, and may be applied to a body tissue such as an external ear canal, a gap between walls in building, a place within piping, and an industrial product having a hollow space. The present invention is versatile in various applications for measurement/observation within a small space which tends to contain blind corners.

The embodiments disclosed herein are only exemplarily and are not construed to limit the present invention. The scope of the present invention is defined by claims, rather than the description herein, and intended to include all equivalents of the claims and modifications made within the scope of the invention.

REFERENCE SIGNS LIST

10: probe, 12: housing, 13: measurement window, 14: mirror, 15: offset mirror, 20: connecting section, 30: optical measurement unit, 40: control unit, 50: display unit, 60: power unit, 80, 80b: handpiece, 82: varifocal unit, 82d: liquid lens, 83: reference unit, 84: light path length adjustment unit, 85, 85d, 85d1, 85d2, 85d3: optical sensor, 86, 93: collimate lens, 88: beam splitter, 91, 92, 95: light guide, 96: imaging lens, 97: diaphragm unit, 98: quarter wavelength plate, 99: dichroic mirror, 100: three-dimensional scanner

The invention claimed is:

1. A three-dimensional scanner for obtaining shape information of an object body, the three-dimensional scanner comprising:
a light source unit;
a detection unit for detecting light from the light source unit, the light being reflected on the object body;
a reference unit for being irradiated with a part of the light from the light source unit that is separate from the light being reflected on the object body;
a lens that controllably and simultaneously changes a focal position of the light from the light source unit to the detection unit via the object body and a focal position of the part of the light from the light source unit to the detection unit via the reference unit, wherein both of the light from the light source unit to the detection unit via the object body and the part of the light from the light source unit to the detection unit via the reference unit travel through the lens at least once;
a light path length adjustment unit for independently adjusting a length of a light path from the reference unit to the detection unit relative to, and based on, a length of a light path from the object body to the detection unit;

a determination unit for determining a condition of the lens based on light that has been reflected on the reference unit and detected by a part of the detection unit; and a calculation unit for calculating shape information of the object body from light detected by the detection unit, using information of the condition of the lens determined by the determination unit.

2. The three-dimensional scanner according to claim 1, further comprising:
a probe for emitting the light from the light source unit to the object body, and for receiving the light reflected on the object body, the probe being detachable from an opening of the three-dimensional scanner,
wherein the reference unit is provided within a housing of the three-dimensional scanner.

3. The three-dimensional scanner according to claim 1, further comprising:
a probe for emitting the light from the light source unit to the object body, and for receiving the light reflected on the object body, the probe being detachable from an opening of the three-dimensional scanner,
wherein the reference unit is provided for the probe.

4. The three-dimensional scanner according to claim 3, wherein
the probe includes an optical element for changing a direction of the light from the light source unit and a direction of the light reflected on the object body, and
the reference unit is provided for a part of the optical element.

5. The three-dimensional scanner according to claim 1, wherein
the detection unit is configured by a single optical sensor, and
a part of the optical sensor detects the light reflected on the reference unit, and a remaining part of the optical sensor detects the light reflected on the object body.

6. The three-dimensional scanner according to claim 1, wherein
the light source unit is configured by a single light source, and
a part of the light source irradiates the reference unit, and a remaining part of the light source irradiates the object body.

7. The three-dimensional scanner according to claim 1, wherein
the light irradiating the reference unit has a predetermined pattern.

8. The three-dimensional scanner according to claim 1, wherein
the light irradiating the reference unit has no predetermined pattern.

9. The three-dimensional scanner according to claim 1, wherein
the reference unit has a surface with a predetermined design pattern.

10. The three-dimensional scanner according to claim 1, wherein
the reference unit has a surface with no predetermined design pattern.

11. The three-dimensional scanner according to claim 1, wherein
the calculation unit calculates the shape information of the object body based on a focusing method.

12. The three-dimensional scanner according to claim 1, wherein
the lens is a varifocal lens that prevents a position of the lens from mechanically moving.

13. The three-dimensional scanner according to claim 1, further comprising:
a diaphragm unit for adjusting light to the detection unit, the diaphragm unit being provided at any position along a light path from the reference unit to the detection unit.

14. The three-dimensional scanner according to claim 1, wherein
the reference unit has a surface to be irradiated with light, the surface having a retardation plate.

15. The three-dimensional scanner according to claim 1, wherein
a wavelength of the light, from the light source unit, irradiating the reference unit is different from a wavelength of the light from the light source unit irradiating the object body.

16. A probe for emitting light from a light source unit to an object body, and for receiving light reflected on the object body, the probe being detachable from an opening of a three-dimensional scanner, the probe comprising:
a reference unit for being irradiated with a part of the light from the light source unit that is separate from light reflected on the object body; and
a housing in which the reference unit is provided,
wherein the three-dimensional scanner includes:
a detection unit for detecting the light from the light source unit, the light being reflected on the object body;
a lens that controllably and simultaneously changes a focal position of the light from the light source unit to the detection unit via the object body and a focal position of the part of the light from the light source unit to the detection unit via the reference unit, wherein both of the light from the light source unit to the detection unit via the object body and the part of the light from the light source unit to the detection unit via the reference unit travel through the lens at least once;
a light path length adjustment unit for independently adjusting a length of a light path from the reference unit to the detection unit relative to, and based on, a length of a light path from the object body to the detection unit;
a determination unit for determining a condition of the lens based on light that has been reflected on the reference unit and detected by a part of the detection unit; and
a calculation unit for calculating shape information of the object body from light detected by the detection unit, using information of the condition of the lens determined by the determination unit.

* * * * *